US009902757B2

(12) United States Patent
Thery et al.

(10) Patent No.: US 9,902,757 B2
(45) Date of Patent: Feb. 27, 2018

(54) DEVICES AND METHODS FOR CONTROLLING ACTIN FILAMENTS GROWTH AND ORGANIZATION USING MICROPATTERNED NUCLEATION SITES

(75) Inventors: Manuel Thery, Grenoble (FR); Laurent Blanchoin, Saint Egreve (FR); Rajaa Paterski, Saint Egreve (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE JOSEPH FOURIER—GRENOBLE 1, Saint Martin d'Heres (FR)

( * ) Notice: Subject to any disclaimer, the term of this patent is extended or adjusted under 35 U.S.C. 154(b) by 1135 days.

(21) Appl. No.: 13/814,637

(22) PCT Filed: Aug. 9, 2011

(86) PCT No.: PCT/EP2011/063676
§ 371 (c)(1),
(2), (4) Date: Feb. 6, 2013

(87) PCT Pub. No.: WO2012/020011
PCT Pub. Date: Feb. 16, 2012

(65) Prior Publication Data
US 2013/0130394 A1    May 23, 2013

(30) Foreign Application Priority Data
Aug. 10, 2010   (EP) .................................... 10305880

(51) Int. Cl.
*G01N 33/68* (2006.01)
*C07K 14/435* (2006.01)
*G01N 33/50* (2006.01)

(52) U.S. Cl.
CPC ....... *C07K 14/435* (2013.01); *G01N 33/6887* (2013.01); *G01N 2333/4712* (2013.01); *G01N 2500/20* (2013.01)

(58) Field of Classification Search
CPC .... G01N 33/6887; G01N 33/68; G01N 33/50; G01N 33/48; C07K 14/435; C07K 14/00; Y10T 436/24; Y10T 436/00
USPC .................. 436/173; 422/131, 129
See application file for complete search history.

(56) References Cited

U.S. PATENT DOCUMENTS

| | | |
|---|---|---|
| 7,955,838 B2 | 6/2011 | Bornens et al. |
| 8,765,472 B2 | 7/2014 | Thery |
| 9,070,702 B2 | 6/2015 | Gabriel et al. |
| 9,250,241 B2 | 2/2016 | Thery et al. |
| 2003/0170726 A1 | 9/2003 | Fradelizi et al. |
| 2005/0106629 A1 | 5/2005 | McGrath et al. |
| 2006/0003399 A1 | 1/2006 | Tomasevic et al. |
| 2014/0024041 A1 | 1/2014 | Tseng et al. |
| 2015/0048513 A1 | 2/2015 | Gabriel et al. |

FOREIGN PATENT DOCUMENTS

| | | |
|---|---|---|
| CN | 103201631 | 7/2013 |
| DE | 10 2007 022 915 | 11/2008 |
| EP | 2 437 063 | 5/2014 |
| JP | 5826844 | 9/2013 |
| WO | WO 2004/036011 | 4/2004 |
| WO | WO 2013/117624 | 8/2013 |

OTHER PUBLICATIONS

Xu, X.-P. et al. "Three-dimensional recontructions of Arp2/3 complex with bound nucleation promoting factors" *The EMBO Journal*, 2012, pp. 236-247, vol. 31, No. 1.
Ti, S.-C. et al. "Structural and biochemical characterization of two binding sites for nucleation-promoting factor WASp-VCA on Arp2/3 complex" *PNAS*, Aug. 16, 2011, pp. E463-E471, vol. 108, No. 33.
Blanchoin, L. et al. "Interactions of ADF/cofilin, Arp2/3 complex, capping protein and profilin in remodeling of branched actin filament networks" *Current Biology*, Oct. 14, 2000, pp. 1273-1282, vol. 10, No. 20.
Achard, V. et al. "A "Primer"—Based Mechanism Underlies Branched Actin Filament Network Formation and Motility" *Current Biology*, Mar. 9, 2010, pp. 423-428, vol. 20, No. 5.
Akin, O. et al. "Capping Protein Increases the Rate of Actin-Based Motility by Promoting Filament Nucleation by the Arp2/3 Complex" *Cell*, May 30, 2008, pp. 841-851, vol. 133, No. 5.
Chen, Z. et al. "Structure and control of the actin regulatory WAVE complex" *Nature*, Nov. 25, 2010, pp. 533-538, vol. 468, No. 7323.
Ferron, F. et al. "Structural basis for the recruitment of profilin-actin complexes during filament elongation by Ena/VASP" *The EMBO Journal*, Oct. 1, 2007, pp. 4597-4606, vol. 26, No. 21.
Yao, L. et al. "Fabrication of semiconductor nanowires by conjugation of quantum dots to actin filaments" *Anal Bioanal Chem*, Sep. 3, 2009, pp. 1563-1566, vol. 395, No. 5.
Patolsky, F. et al. "Actin-based metallic nanowires as bio-nanotransporters" *Nature Materials*, Oct. 1, 2004, pp. 692-695, vol. 3, No. 10.
Campellone, K. G. et al. "A nucleator arms race: cellular control of actin assembly" *Nature Reviews, Molecular Cell Biology*, Apr. 1, 2010, pp. 237-251, vol. 11, No. 4.
Sundberg, M. et al. "Actin Filament Guidance on a Chip: Toward High-Throughput Assays and Lab-on-a-Chip Applications" *Langmuir*, Aug. 1, 2006, pp. 7286-7295, vol. 22, No. 17.
Galland, R. et al. "Fabrication of three-dimensional electrical connections by means of directed actin self-organization" *Nature Materials*, Feb. 10, 2013, pp. 416-421, vol. 12, No. 5.

(Continued)

*Primary Examiner* — Christine T Mui
(74) *Attorney, Agent, or Firm* — Saliwanchik, Lloyd & Eisenschenk

(57) ABSTRACT

The present invention concerns devices and methods for controlling actin filament growth and organization with micropatterned nucleation sites, and their uses for studying actin network formation, for screening of drugs or for preparing complex structures.

23 Claims, 9 Drawing Sheets

(56) References Cited

OTHER PUBLICATIONS

Written Opinion in International Application No. PCT/EP2013/052393, dated Jun. 12, 2013, pp. 1-8.
Yi, J. et al. "Engineering an artificial amoeba propelled by nanoparticle-triggered actin polymerization" *Nanotechnology*, 2009, pp. 1-8, vol. 20, No. 8.
Database Biosis [Online] Accession No. PREV200400126365, Fisher, C. et al. "Micropatterning of ActA to study actin-based motility" Jan. 2004, p. 1, vol. 86, No. 1.
Nakamura, H. et al. "Shape Control of Filamentous Motor Proteins for Bio-Nano Driving Units" *IEEE $20_{th}$ International Conference on Micro Electro Mechanical Systems*, Jan. 21-25, 2007, pp. 409-412, XP031203731.
Wong, T. et al. "Manufacture of Nanoscale Structures through Integrated Top-down and Bottom-up Approaches" *Proceedings of the $7^{th}$ IEEE International Conference on Nanotechnology*, Aug. 2-5, 2007, XP031307738, pp. 126-130.
Yi, J. et al. "Microsphere Dynamics for Actin Based Nanorobotic Motility" *Nanotechnology*, Aug. 12, 2003, pp. 725-728, vol. 2.
Roos, W. et al. "Freely Suspended Actin Cortex Models on Arrays of Microfabricated Pillars" *Chemphyschem*, 2003, pp. 872-877, vol. 4.
Michelot, A. et al. "Actin-Filament Stochastic Dynamics Mediated by ADF/Cofilin" *Current Biology*, May 15, 2007, pp. 825-833, vol. 17.
Uhrig, K. et al. "Optical force sensor array in a microfluidic device based on holographic optical tweezers" *Lab on a Chip*, 2009, pp. 661-668, vol. 9.
Written Opinion in International Application No. PCT/EP2011/063676, dated Oct. 10, 2011, pp. 1-8.
Mullins, R. D. et al. "The interaction of Arp2/3 complex with actin: Nucleation, high affinity pointed end capping, and formation of branching networks of filaments" *Proc. Natl. Acad. Sci.*, May 1998, pp. 6181-6186, vol. 95.
"Actin assembly-inducing protein" Wikipedia Encyclopedia, 2013, accessed Feb. 18, 2013, http://en.wikipedia.ort/wiki/Actin_assembly-inducing_protein.

Actin growth with pWA adsorption

Actin growth without pWA adsorption

Experiment                                    Model

Fig. 5e
Fig. 5f
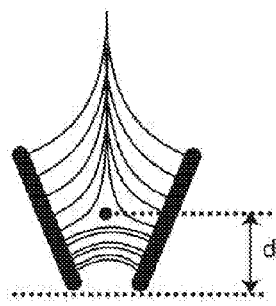
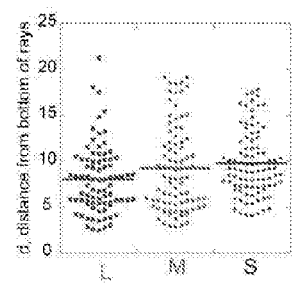
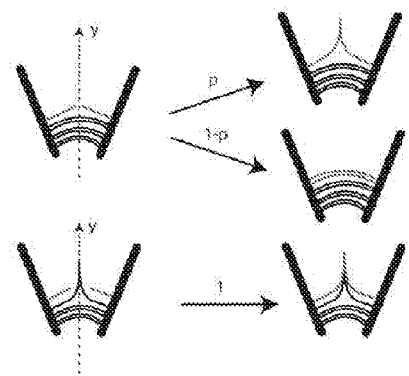
Fig. 5g
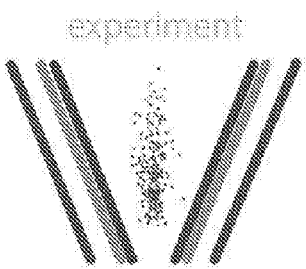
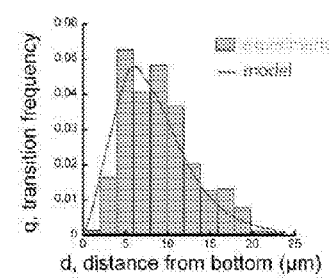
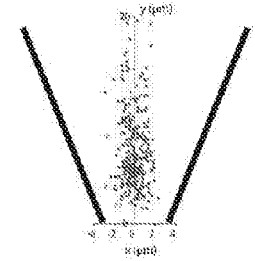
Fig. 5h
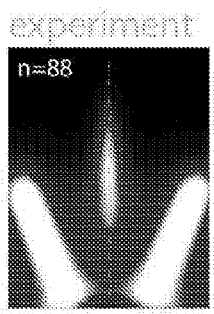
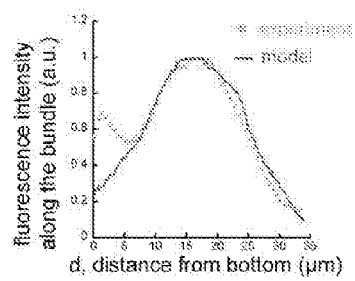
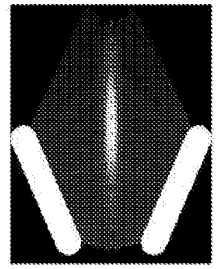

Fig 6a Addition over performed structure : bundling of adjacent filaments within ordered architecture
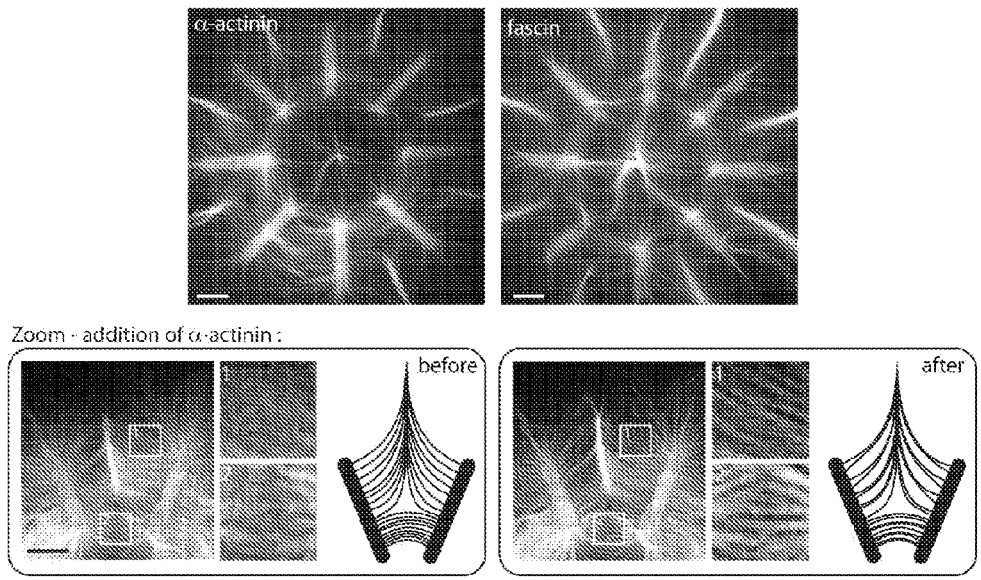
Fig 6b Addition from the start : dose dependant response with loss of standard organization
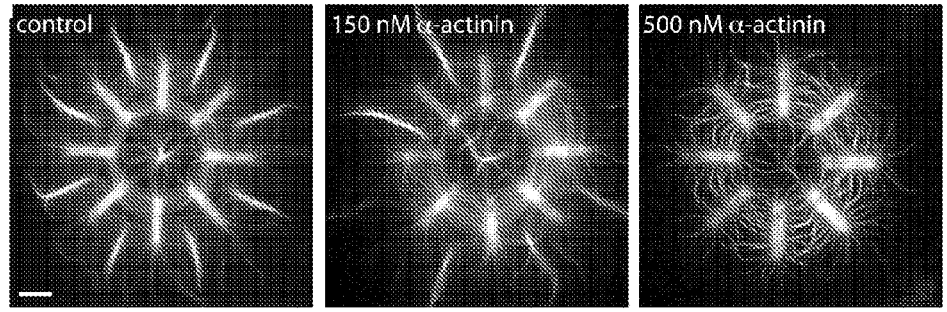
Fig 6c α-actinin bundling activity
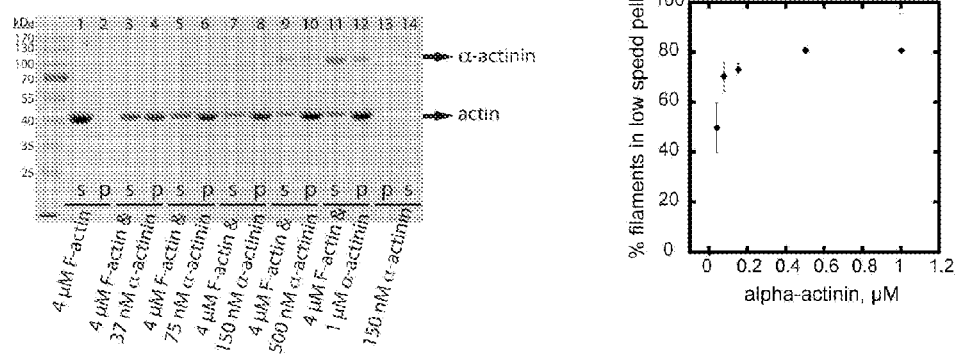

Fig 6d
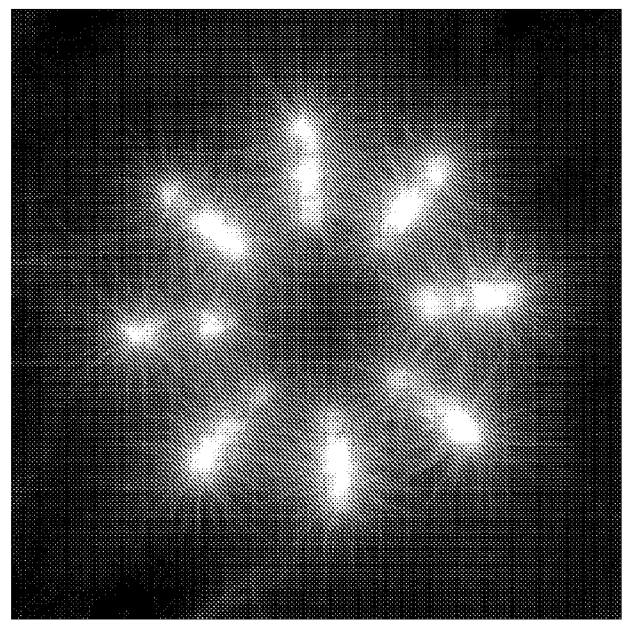
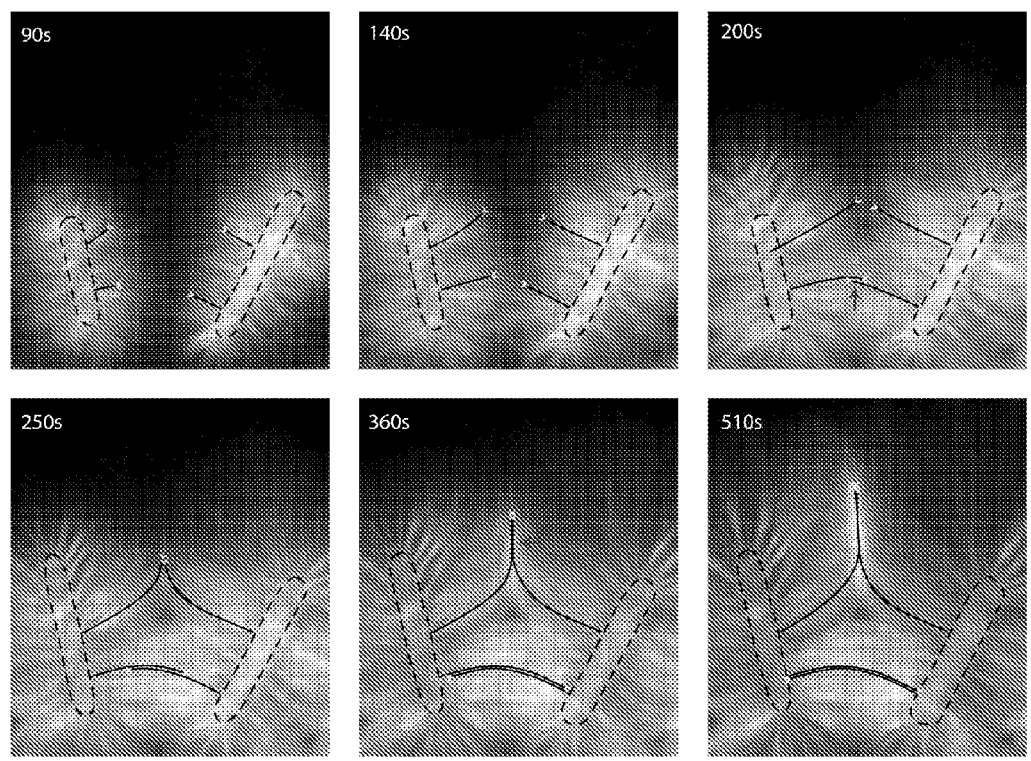
FIGURE 7

DEVICES AND METHODS FOR CONTROLLING ACTIN FILAMENTS GROWTH AND ORGANIZATION USING MICROPATTERNED NUCLEATION SITES

CROSS-REFERENCE TO RELATED APPLICATION

This application is the U.S. national stage application of International Patent Application No. PCT/EP2011/063676, filed Aug. 9, 2011.

The Sequence Listing for this application is labeled "Seq-List.txt" which was created on Feb. 2, 2013 and is 4 KB. The entire contents of the sequence listing is incorporated herein by reference in its entirety.

FIELD OF THE INVENTION

The present invention relates to devices and methods for controlling actin filament network organization, and thereby for studying actin filament network organization, for screening compounds for their ability to modulate actin network organization or for manufacturing actin-based components, in particular for using the actin network as a template for further nano-engineering processes.

BACKGROUND OF THE INVENTION

Actin filaments constitute one of the main components of the cell cytoskeleton. Actin filaments are polymers which spontaneously self-assemble into cells from actin monomers. They form complex intracellular structures, providing mechanical support for regulating cells' shape. Assembled into bundles in filopodia, or in stress fibres, they play a pivotal role during cell morphogenesis, adhesion and motility. The bundles' emergence has been extensively related to specific actin regulators in vivo. Such dynamic modulation was also highlighted by biochemical reconstitution of actin network assembly, in bulk solution or with biomimetic devices. However, the question of how geometric boundaries, such as those encountered in cells, affect the dynamic formation of highly ordered actin structures has not been examined.

Monomers of actin can be isolated and purified from filtrated cellular homogenates. In vitro, these monomers can polymerize in the presence of nucleation proteins and ATP (energy source), forming new actin filaments (F-actin). Unlike intracellular assemblies, the filaments network has no particular structure when formed in vitro. Several methods have been described for recreating an actin network in vitro (Haraszti et al., 2009).

In a first approach, the in vitro polymerization of actin filaments is performed in solution from purified monomers (e.g., US2004/0038323, US2006/0003399). However, this type of reconstitution suffers from spontaneous and random organization of the filaments network, in particular the complete lack of geometric control of the initiating regions.

In a second approach, the actin polymerization is performed with beads coated with nucleating proteins dispersed in a solution (Michelot et al., 2007). However, one of the major limitations of these coated beads is their random relative positions in solution.

In a third approach, the filaments' organization is controlled after their polymerization in a solution.

For instance, they may be immobilized on a pillar network (i.e., the actin filaments are put in a line with the pillar network) (Roos et al., 2003). Arrays of 2-micron-wide gold discs were fabricated on top of 20-micron-high pillars. These dots were used to graft myosin and thereby attach actin filaments. These attached filaments were then elongated using a solution comprising actin monomers. Long filaments growing out of the dots were not oriented and the network was not spontaneously organized in space. But the addition of filamin, an actin associated protein, could force filament bundling and induce the formation of bridges between the dots. This organization could occur only when filaments were anchored on top of micro-pillars, whose length has to exceed the filaments' length. The same array of dots on a flat surface, rather than on top of pillars, only promotes the formation of an ill-defined network even in the presence of filamin.

They may also be sent in a chamber where beads with optical traps are placed (Uhrig et al., 2009).

However, in these two cases, the actin filament network is not self-assembled; it is externally oriented by fluid flow or capturing beads' positions. The final architecture does not rely on biological properties of actin filaments assembly and interactions, so these methods cannot be used to test these properties. In addition, in the filament bundles that are externally oriented, the polarity of individual filament is not controlled. The precise architecture of these networks is therefore not highly controlled.

In a fourth approach, the filaments' organization is controlled on a solid support by introducing on a surface an actin nucleation site and an actin capture site (US20050106629). With these two anchorage points, the filaments' organization may be controlled. However, the structure is not self-assembled but externally arranged by the controlled location of nucleation and capture sites. In particular, the nucleation sites are arranged on the support so that the actin filaments from one nucleation site do not interact with actin filaments from another nucleation site. In addition, filament growth out of the nucleation site is not oriented and has to be externally driven by beads, or manipulated by a magnetic or optical trap.

None of these approaches provide self-assembling of an ordered actin filament network with reproducible and controlled geometry.

SUMMARY OF THE INVENTION

The inventors demonstrated for the first time that the nucleation geometry in itself can be the principal determinant of the architecture of actin filaments. The inventors defined the rules directing the actin filament organization, the first rule being the radial growth of the actin filament in regards to the nucleation site. They developed micro-patterns of actin nucleation sites, allowing the preparation of interesting and reproducible actin filaments network structures. In particular, shape, orientation and distance between nucleation regions control filament orientation and length, filament-filament interactions and filopodia-like bundle formation (parallel bundle) or stress fiber-like bundle formation (antiparallel bundle).

Therefore, the present invention provides a device comprising a surface having disposed thereon a pattern, preferably a nano- or micro-pattern, comprising a line (e.g. at least one line) comprising an actin nucleation agent or a pattern comprising at least two dots, wherein each dot comprises an actin nucleation agent and the dots are at a distance suitable for allowing the interaction of the polymerized actin filaments from two adjacent dots. Preferably, the line has a minimal length of 15, 20, 25 or 30 microns, preferably 15 or 20 microns. Preferably, the dots have a diameter of from 1 to 10 μm, preferably from 2 to 7 μm, more preferably about 5 μm. Preferably, the surface has disposed thereon a plurality of patterns, preferably a plurality of addressable patterns.

Preferably, the actin nucleation agent is selected from the group consisting of members of the WASP/SCAR family, PWA fragments thereof and VCA domains thereof, and ActaA, IscA and C-terminal regions thereof. More preferably, the actin nucleation agent is pWA. Optionally, said pWA is linked or fused to one or two tags (e.g., a GST tag and/or a His tag). More particularly, said pWA is linked or fused to a GST tag at its N-terminal end and an His tag at its C-terminal end.

Preferably, the pattern comprises several dots or lines, the dots or lines being at a distance suitable for allowing the interaction of the polymerized actin filaments from two adjacent dots or lines. Accordingly, the pattern may include at least 2, 3, 4, 5, 6, 7, 8, 9 or 10 lines or dots, in particular may include 2, 3, 4, 5, 6, 7, 8, 9 or 10 lines or dots. Preferably, the distance between two adjacent lines or dots (i.e., the proximal ends of two adjacent lines) is 1, 2, 5, 10, 15, 20, 25 or 30 microns, preferably 5, 10, 15 or 20 microns, more preferably of about 10 microns.

Preferably, the pattern, preferably a nano- or micro-pattern, comprises:
  one circle or several circles, preferably nested circles;
  two or more lines; and/or
  an array of dots.

In a preferred embodiment, the pattern, preferably a nano- or micro-pattern, comprises two to five circles, said circles having different diameters and being concentric or eccentric. Preferably, the circles are nested; in other words, the smaller circles are contained into the bigger circles.

In a first alternative preferred embodiment, the pattern, preferably a nano- or micro-pattern, comprises two or more lines, in particular two or more straight lines, being parallel or forming an angle of less or no more than 25° with respect to each other, preferably less or no more than 22° with respect to each other, more preferably less or no more than 10° with respect to each other.

In a second alternative preferred embodiment, the pattern, preferably a nano- or micro-pattern, comprises two or more lines, in particular two or more straight lines, forming an angle of more than 25, 30, 35, 40 or 45° with respect to each other and less than 110°, preferably between 45° and 90° with respect to each other. Optionally, the pattern includes two lines, preferably two straight lines. Optionally, the pattern includes several lines arranged so as to form a radial pattern.

In a third alternative preferred embodiment, the pattern, preferably a nano- or micro-pattern, comprises two or more lines, in particular two or more straight lines, forming an angle of more than 110° and less than 150°, 140° or 130°, preferably between 110° and 120° with respect to each other. Optionally, the pattern includes two linear actin nucleation sites, preferably two straight linear actin nucleation sites. Optionally, the pattern includes several linear actin nucleation sites arranged so as to form a radial pattern.

Preferably, the surface is silicon, strained silicon, polycrystalline silicon, silicon dioxide, germanium, gallium arsenic, glass, plastic, ceramic, or metal. In a preferred embodiment, the surface is glass. In a more preferred embodiment, the surface is planar.

The present invention also relates to a kit comprising a device as disclosed herein and an actin polymerization mix comprising components sufficient to induce actin polymerization. The components comprise actin monomer(s), ATP, a Arp2/3 complex, an actin filament and divalent cation.

Optionally, the actin polymerization mix may further comprise profilin. Optionally, the polymerization mix comprises labeled actin monomer(s), in particular actin monomer(s) labeled with fluorescent dye or protein and/or actin monomer(s) bound to a metal atom, in particular with gold.

The present invention further relates to a method for preparing or manufacturing actin filaments network comprising a) providing a device as disclosed herein; b) contacting said pattern, preferably said nano- or micro-pattern, with a polymerization solution or mix comprising actin monomer(s), ATP, divalent cation, an actin filament and a Arp2/3 complex, thereby inducing polymerization of actin filaments; and optionally c) removing the polymerization solution or mix. The method may further comprise a step of removing the obtained actin filaments from the surface. The method may further comprise the coating of the actin filaments, in particular coating with a conductive substance such as gold, and/or the treatment of the actin filaments, in particular with an actin cross-linking agent such as fascin or alpha-actinin. Preferably, the polymerization solution or mix contains an amount of the Arp2/3 complex sufficient to induce the polymerization of a critical density of actin filaments, in particular at least 30 nM of the Arp2/3 complex.

In addition, the present invention provides a method for studying the spatial organization of actin filaments networks, wherein the method comprises a) providing a device as disclosed herein; b) contacting said pattern, preferably said nano- or micro-pattern, with a polymerization solution or mix comprising actin monomer(s), ATP, divalent cation, an actin filament and a Arp2/3 complex, thereby inducing polymerization of actin filaments; and c) observing the actin filaments networks. Preferably, the polymerization solution or mix contains an amount of the Arp2/3 complex sufficient to induce the polymerization of a critical density of actin filaments, in particular at least 30 nM of the Arp2/3 complex.

The present invention also relates to a method for screening a test molecule for its capacity to modulate the actin filaments networks, wherein the method comprises a) providing a device as disclosed herein; b) contacting said pattern, preferably said nano- or micro-pattern, with a polymerization solution or mix comprising actin monomer(s), ATP, divalent cation, an actin filament and a Arp2/3 complex, thereby inducing polymerization of actin filaments; and c) observing the actin filaments networks, wherein the test molecule is added before, during the actin polymerization and/or after the actin polymerization and wherein the effect of the test molecule on the actin filaments networks is determined. Preferably, the polymerization solution or mix contains an amount of the Arp2/3 complex sufficient to induce the polymerization of a critical density of actin filaments, in particular at least 30 nM of the Arp2/3 complex.

Finally, the present invention relates to a method for studying molecular motors, for example myosins, the method comprising a) providing a device as disclosed herein; b) contacting said pattern, preferably said nano- or micro-pattern, with a polymerization solution or mix comprising actin monomer(s), ATP, divalent cation, an actin filament and a Arp2/3 complex, thereby inducing polymerization of actin filaments; and c) observing the structure, interactions and/or deformation of the polymerized actin filaments, wherein the molecular motor is added before, during the actin polymerization and/or after the actin polymerization. Preferably, the polymerization solution or mix contains an amount of the Arp2/3 complex sufficient to induce the polymerization of a critical density of actin filaments, in particular at least 30 nM of the Arp2/3 complex.

Optionally, a test molecule may also be added simultaneously or sequentially with the molecular motor and the effect of the test molecule on the structure and the deformation of the polymerized actin filaments is observed. Optionally, the method may further comprise the selection of a test molecule which is able to modulate the activity of the molecular motor and its interaction with actin filaments.

BRIEF DESCRIPTION OF THE DRAWINGS

FIG. 1a, surface micropatterning method. FIG. 1b, epifluorescence microscopy images of actin filaments nucleated on the pWA-coated micropattern, and of spontaneous filament polymerization in the solution in absence of pWA-coating.

FIG. 2a, initiation and propagation of actin-Alexa 568 assembly along a pWA-coated micropattern followed by evanescent wave microscopy. FIG. 2b, variation of the monomeric actin concentration present in the medium. Actin filaments elongating out of the nucleation area were longer with an increasing actin concentration. FIG. 2c, variation of the nucleation factor, the Arp2/3 complex concentration. Actin filaments escaping the nucleation area became shorter with an increasing concentration of the Arp2/3 complex. FIG. 2d, response to the barbed end capper, the heterodimeric capping protein. Actin filaments escaping the nucleation area shortened with an increasing concentration of capping protein. FIG. 2e, polymerization of the actin monomer-Ca-ATP rather than the physiologically relevant form, actin monomer-Mg-ATP. In the standard conditions of actin assembly, calcium actin filaments grew unperturbed from the nucleation micro-patterned surfaces. FIG. 2f, actin polymerization in the presence of 0.25% methylcellulose. FIG. 2g, actin polymerization in the presence of 1% methylcellulose. In both cases filaments kept their assembling properties into bundles. Scale bars are 20 μm.

FIG. 3a, fluorescent microscopy images of actin structures formed on nucleation circles. FIG. 3b, actin network density maps calculated by overlaying and averaging several images (first column) and from numerical simulations of actin filament growth (third and fourth columns). Nucleation regions are represented. The inventors measured the fluorescence ratio of linescans along inner and outer circles as in the inset image (second column, dashed circles). Dots correspond to ratios of the experimental density maps (second column); lines refer to ratios of the numerical simulations (third and fourth columns) where actin filaments can or cannot cross the dense actin network. Scale bars indicate 10 μm.

FIG. 4a, nucleation, elongation and deformation of actin filaments nucleated on a 120° V-shaped nucleation zone. FIG. 4b, fluorescence microscopy images of actin structures formed on V-shaped zones with four different angles. FIG. 4c, average fluorescent projection of 30 images for each angle. FIG. 4d, schematic representation of bundle formation resulting from the interaction of actin filaments nucleated on the micropattern. The fluorescent intensity distribution along the linescans (dotted lines) was performed on the averaged images; the arrow, in panel c, indicates the maximum fluorescence. Scale bars indicate 10 μm.

FIGS. 5a-5h: Intrinsic properties and collective assembly of actin filaments regulate parallel bundle formation. FIG. 5a, time-lapse acquisition of the nucleation and elongation of actin filaments on an eight-branched radial array. FIG. 5b, fluorescence images of three sizes of the radial array at steady state of actin assembly. FIG. 5c, average fluorescent projections. FIG. 5d, a zoom of FIG. 5b. FIG. 5e, the distance d between the bottom of the bar and the position of the transition point did not vary between the three radial array sizes. FIG. 5f, model assumptions: actin filaments' probabilistic comportment depends on their local environment. FIG. 5g, left: combined experimental measures from FIG. 5e for the three different radial array sizes. Right: 200 transition point positions calculated from the probability Q(y) and a normal variability along the X axis. Middle: comparison of experimental measures of the transition point position and the model function Q(y). FIG. 5h, left: average fluorescent projection of each sector of the large radial array. Right: the calculated fluorescent intensity of 10,000 parallel filaments constituting the bundle generated according to the function Q(y). Middle: comparison of fluorescent intensity along the bisecting line on experimental averaged image (dots) and on the analytical formulation obtained from the model. Scale bars indicate 10 μm.

FIGS. 6a-6d: Differential effect of bundling proteins on geometrically induced actin networks. FIG. 6a, effect of the addition of α-actinin or fascin over performed filamentous structures on patterned surface. In order to introduce the protein without perturbing the organization of actin filaments, a special setup was used. Instead of creating a flow cell, actin polymerization mix was dropped directly on the micropatterned coverslip and kept in a humid chamber. Droplets of bundling proteins could then gently be added on top of it. This addition of 1 μM α-actinin leads to the bundling of adjacent filaments within the ordered architecture (zoomed images) whereas 1 μM fascin induces no change. FIG. 6b, images showing the effect of an addition of alpha-actinin from the start. Standard organization of filaments is lost at high concentrations. FIG. 6c, α-actinin bundles actin filaments. Low-speed pelleting assay was performed at 13 krpm at 4° C. of 4 μM actin assembled to steady state for 1 hour at 20° C. in the presence or not of α-actinin as indicated. Unbundled actin filaments remained in the supernatant (lanes 1 and 2) whereas α-actinin-bundled filaments were transferred to the pellet (lanes 3 to 12). The percentage of actin filaments recovered in the low-speed pellet as a function of the concentration of α-actinin shows that the α-actinin binds to actin filaments with an apparent Kd of 20 nM. FIG. 6d, images showing the effect of an addition of fascin (100 nM) from the start. Standard organization of filaments is lost at this concentration.

FIG. 7: Real-time acquisition of parallel and anti-parallel filament networks formation observed by TIRF microscopy. Actin filament assembly was initiated from two nucleation bars (dotted ovoid areas). Lines highlight the orientation of actin filaments emanating from the branched actin network initiated on the nucleation area. Small inverted arrowhead indicates the elongating barbed end position. Large arrows point out the anti-parallel (at 200 s) or the parallel (at 360 s) actin filaments network formation.

DETAILED DESCRIPTION OF THE INVENTION

Figure 1A:
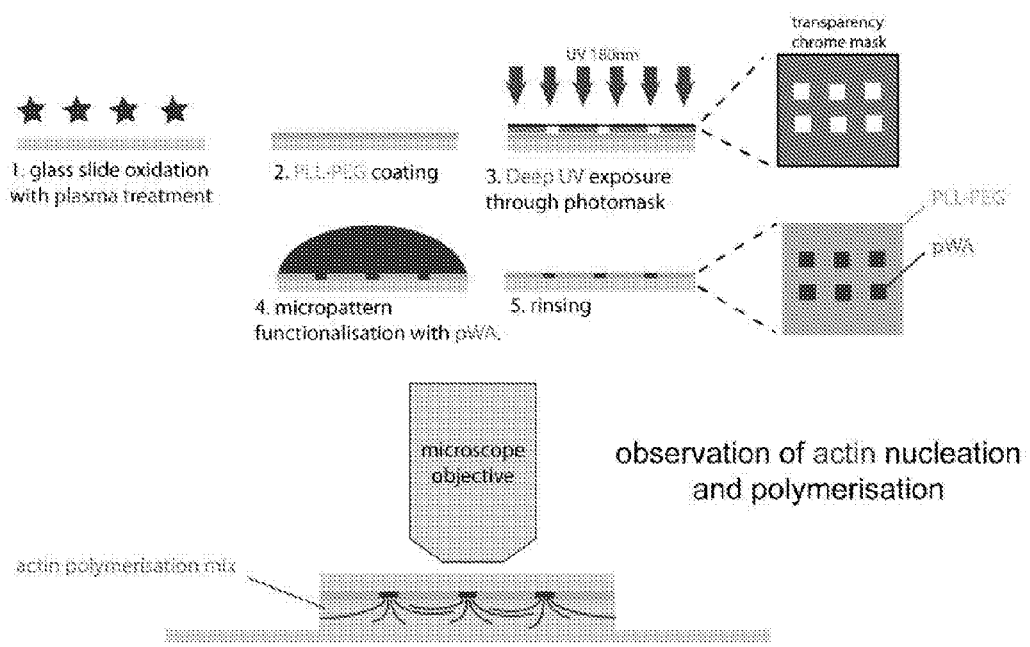
FIGS. 1a-1b: Geometric control of actin nucleation and growth.

The inventors defined the rules directing the spatial self-organization of actin filaments, the first rule being the radial growth of the actin filaments in regards to the nucleation site, with their barbed ends distally oriented. They developed micro-patterns of actin nucleation sites, allowing the preparation of interesting and reproducible actin filaments network structures. In particular, shape, orientation and distance between nucleation regions control filament orientation and length, filament-filament interactions and filopodia-like or stress fiber-like bundle formation.

By "self-organization" it is intended herein that the intrinsic physico-chemical properties of actin filaments promote their interaction and spatial rearrangement. Filaments will cross over or change their original orientation and align in parallel or anti-parallel fashion. These orientation processes of actin filaments do not require outside intervention (including an experimenter, an external material, or an actin capture site).

The pattern allows the polarization of the actin filaments. For all the actin filaments, the barbed ends are distally oriented.

By "actin filaments networks", "actin filaments network architecture" or "actin filaments organization" is intended herein the spatial positioning of actin filaments with respect to each others, i.e., the geometry adopted by the filaments in the network they form. Through actin filament interactions, they form bundles of actin filaments. In particular, depending on the pattern, it provides parallel actin filaments, anti-parallel actin filaments, bundles of parallel actin filaments, bundles of antiparallel actin filaments, etc. By "parallel interactions of actin filaments" is intended that the filaments present the same polarity. By "antiparallel interactions of actin filaments" is intended that the filaments present an opposite polarity. In addition, the orientation of the bundles can be controlled by the patterns. These patterns are therefore very useful because they provide reproducible and predictable structures or networks of actin filaments.

The present invention relates to surfaces suitable for preparing actin filaments and methods of using them. Depending on the patterns formed, the surface disclosed herein can form very thin structures (as thin as a single actin filament, approximately 7-8 nm) or larger structures when the patterns lead to bundles of actin filaments (e.g., 90-100 nm). Additionally, structures with multiple filaments can be shaped to form, for example, columns. Thus, the present invention provides methods and compositions for forming a variety of ordered structures on the micron and nanometer scale for manufacturing and other purposes.

The present invention provides a device comprising a surface having disposed thereon a pattern, preferably a nano- or micro-pattern, comprising a line (e.g. at least one line) comprising an actin nucleation agent or a pattern comprising at least two dots comprising an actin nucleation agent, the dots being at a distance suitable for allowing the interaction of the polymerized actin filaments from two adjacent dots. In particular, the surface has disposed thereon a plurality of patterns, preferably a plurality of addressable patterns. By a plurality of addressable patterns is intended that the patterns have distinct known locations which are recorded and can be accessed on the surface. The knowledge of the precise location of each pattern's location makes these "addressable" patterns useful for a high-throughput assay. Preferably, the pattern is a nano- or micro-pattern. More preferably, the pattern is a micropattern. Preferably, the patterns on the surface are identical. Alternatively, the surface may also comprise several series of different patterns. Preferably, when the surface comprises several patterns, the patterns are disposed thereon at a distance so that there is no interaction of actin filaments between two patterns.

Pattern

First of all, by "pattern" is intended a pattern at the nanometer or micrometer scale. Accordingly, the term "pattern" may be replaced by "nanopattern" or "micropattern". More preferably, the pattern is a micropattern.

It is important to note that, in the present invention, there is no need of an actin capture site on the surface. Indeed, the organization and interactions of actin filaments and the structure formed therewith is controlled by the geometry of the patterns of actin nucleation agent. Accordingly, in a preferred embodiment, the surface has no actin capture site disposed thereon. By actin capture site is intended in particular an actin capture agent selected from the group of myosin, N-ethylmaleimide-myosin, phalloidin, alpha-actinin, and fascin.

In a first embodiment, the surface may have disposed thereon a pattern, more precisely a nano- or micro-pattern, comprising one or several lines comprising or made of the actin nucleation agent. The lines may be straight or curved, or a combination thereof. The lines may be open or closed. The lines, open or closed, may form any geometric form or figure. Of course, some geometric forms or figures may present more interesting features than others (e.g., in terms of actin filaments network structures). One can contemplate patterns forming or comprising circles, squares, lozenges, triangles, ellipses and combinations thereof. The line has a minimal length of 15, 20, 25 or 30 microns, preferably 15 or 20 microns. The length of a line is at least three times its thickness. When a pattern includes several lines, the lines are disposed at a distance suitable for allowing the interaction of the polymerized actin filaments.

The line thickness can be adapted by one skilled in the art and may be for instance 0.05-100 µm. Lines with a thickness of 50-100 nm may provide more precise structures. Lines with a large thickness may also be contemplated. However, an appropriate thickness can be from 1 to 10 µm, preferably from 2 to 7 µm, more preferably about 5 µm.

In a particular, the linear pattern, more precisely the nano- or micro-pattern, includes one or several circles. The pattern with several circles provides the interactions between inward- and outward-growing filaments, thereby forming short and thin anti-parallel bundles between adjacent circles. The distance between nucleating regions can be varied using eccentric circles or kept constant with concentric circles. Illustrating micropatterns of this type are detailed in the Examples section and shown in FIG. 3. Optionally, the pattern, more precisely the nano- or micro-pattern, is formed of one circle. Alternatively, the pattern, more precisely the nano- or micro-pattern, is formed of several circles (e.g., 2, 3, 4, 5, 6, 7, 8, 9 or 10 circles). In particular, the pattern, more precisely the nano- or micro-pattern, is formed of 2, 3 or 4 circles, preferably 3 circles. Preferably, the circles have different diameters and the smaller circles are contained in the bigger circles. The circles may be concentric. Alternatively, the circles may be eccentric. The pattern, more precisely the nano- or micro-pattern, can also be formed of a mixture of concentric and eccentric circles. Preferably, the concentric or eccentric circles are spaced 5, 10, 15, 20, 25 or 30 microns apart, preferably 10, 15 or 20 microns, still more preferably about 15 microns. Preferably, the circle or the smallest circle has a minimum diameter of 15, 20 or 25 microns, preferably 20 microns.

In another particular embodiment, the linear pattern, more precisely the nano- or micro-pattern, contains two or more lines (e.g., 2, 3, 4, 5, 6, 7, 8, 9 or 10 lines), in particular two or more straight lines. The lines may have any convenient length. In particular, the lines may have a length of 10-100 microns, preferably 20-50 microns, more preferably 20-30 microns.

The linear pattern, more precisely the nano- or micro-pattern, may contain one line. This pattern allows a parallel network of actin filaments to be obtained. Illustrating micropatterns of this type are detailed in the Examples section and shown in FIGS. 1*b-d* and 2*a-e*.

The two or more lines, in particular two or more straight lines, may be parallel or almost parallel (i.e., an angle of less or no more than 25°, preferably less than 10°). It has been determined by the inventors that such a pattern of lines provides filaments associated into short and thin anti-parallel bundles. Illustrating micropatterns of this type are detailed in the Examples section and shown in FIGS. 4*b-d* and 5*f*. In particular, the two or more lines, in particular two or more straight lines, may form an angle of 10-25° with respect to each other. In a very particular embodiment, the two or more lines, in particular two or more straight lines, form an angle of about 22° with respect to each other. In particular, the pattern, more precisely the nano- or micro-pattern, includes two lines, preferably two straight lines. The lines are spaced 5, 10, 15, 20, 25 or 30 microns apart, preferably 5, 10, 15 or 20 microns, more preferably of about 10 microns.

Alternatively, the two or more lines, in particular two or more straight lines, may form an angle of more than 25, 30, 35, 40 or 45° and less than 110° with respect to each other. In a preferred embodiment, the angle is between 45° and 90° with respect to each other. It has been determined by the inventors that such a pattern of lines provides a mixed structure with two distinct types of organization: at the proximal part of the lines, filaments associated into short and thin anti-parallel bundles; at the distal part of the lines, a bundle of parallel filaments, in particular on the bisecting line between adjacent lines. The lines are spaced apart in their proximal part by 1, 2, 5, 10, 15, 20, 25 or 30 microns, preferably 5, 10, 15 or 20 microns, more preferably of about 10 microns. Illustrating micropatterns of this type are detailed in the Examples section and shown in FIGS. 4*b-d*, 5, 6 and 7. In particular, the pattern, more precisely the nano- or micro-pattern, includes two lines, preferably two straight lines. The pattern, more precisely the nano- or micro-pattern, may also include several lines arranged so as to form a radial pattern. Accordingly, such a radial pattern may comprise 4-9 lines, preferably 4-8 lines. Preferably, the angles between two adjacent lines in a radial pattern are almost the same (e.g., a 4-branched radial array with an angle of 90°, a 5-branched radial array with an angle of 72°, a 6-branched radial array with an angle of 60°, a 7-branched radial array with an angle of 51°, or an 8-branched radial array with an angle of 45°). Alternatively, the angles between two adjacent lines in a radial pattern may be different. Optionally, they may differ but stay in the same range of angles (i.e., between 25, 30, 35, 40 or 45° and 110°, preferably between 45° and 90°). Optionally, they may differ so as to include different kind of organization or structure. Accordingly, the radial pattern may include lines with an angle between 25, 30, 35, 40 or 45° and 110°, preferably between 45° and 90°.

Additionally, the two or more lines, in particular two or more straight lines, may form an angle of more than 110°. However, the angle is preferably less than 150°, 140° or 130°. It has been determined by the inventors that such a pattern of lines provides a bundle of parallel filaments on the bisecting line between adjacent lines. Illustrating micropatterns of this type are detailed in the Examples section and shown in FIG. 4. In a preferred embodiment, the angle is between 110° and 120° with respect to each other. In particular, the pattern, more precisely the nano- or micro-pattern, includes two lines, preferably two straight lines. The pattern, more precisely the nano- or micro-pattern, may also include several lines arranged so as to form a radial pattern. For instance, such a radial pattern may comprise 3 lines. Preferably, the angles between two adjacent lines in the radial pattern are almost the same (e.g., 120°). The lines are spaced apart in their proximal part by 1, 2, 5, 10, 15, 20, 25 or 30 microns, preferably 5, 10, 15 or 20 microns, more preferably of about 10 microns.

Optionally, the invention also relates to a radial pattern having angles between two adjacent lines that differ so as to include a different kind of organization or structure. Accordingly, the radial pattern may include lines with an angle of the first type (i.e., with an angle of less or no more than 25°), the second type (i.e., with an angle of between 25, 30, 35, 40 or 45° and 110°, preferably between 45° and 90°) and/or the third type (i.e., with an angle of more than 110°).

Figure 8:
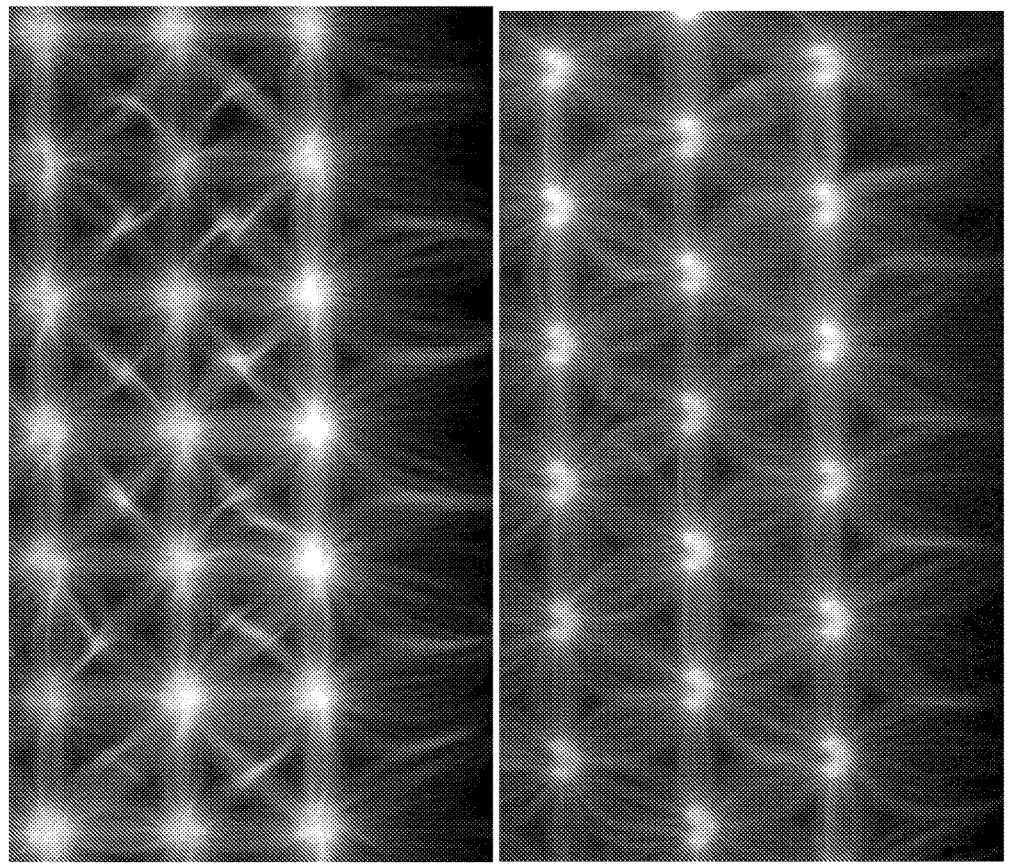
FIG. 8: Actin filaments networks of an array of dots. Actin filaments assembly was initiated from an array of dots of the actin nucleation agent pWA. The diameter of the dots is 5 microns and the dots are spaced of 20 microns. The use of arrays of dots leads to a specific and reproducible actin filaments network. The actin filaments bundles are antiparallel arrangements of actin filaments.
Figure 9:
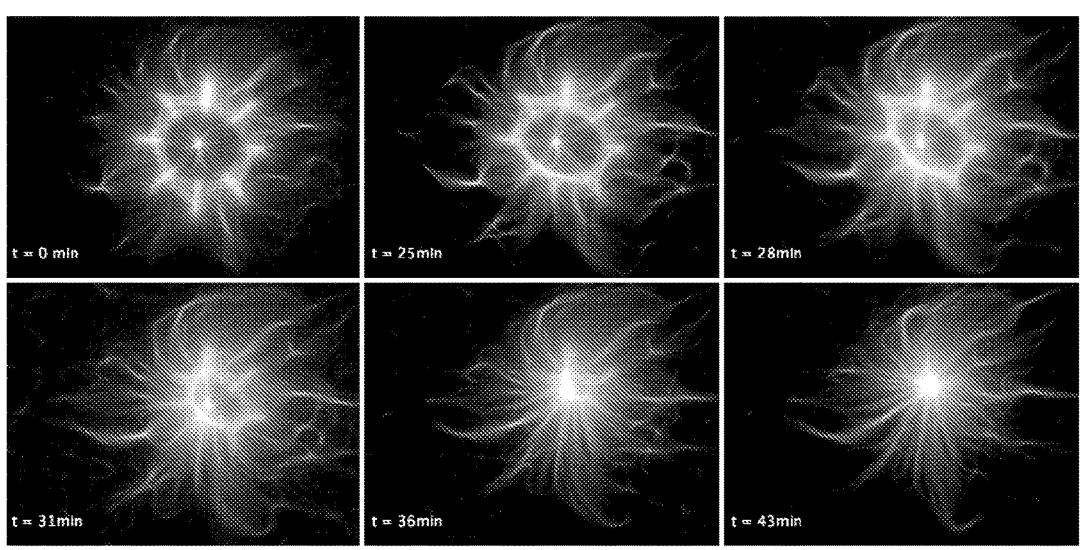
FIG. 9: Study of the effect of a molecular motor on the actin filaments networks based on a radial pattern of nucleation agent. A polymerization mix was added to a radial pattern of 8 bars forming a 45° angle. Actin filaments formed the expected anti-parallel bundles in the proximal part of the bars, and the parallel bundles in the distal one. To test the role of Myosin VI, a molecular motor, on the preformed structure, 10 nM of purified double-headed Myosin VI (DeLaCruz et al., 2001) was added to the mix after complete filament polymerization. The effect was monitored in time-lapse video-microscopy by taking one image of Alexa 488-labeled actin filaments every minute. Images show the contraction of the bottom part of the structure, suggesting that anti-parallel filaments were slid along each other by the molecular motors. Then, after a few minutes, the contraction propagates to the rest of the structure, resulting in the coalescence of all filaments in a purely radial structure made of only parallel bundles. This experiment highlights the actual contractile effect of Myosin VI on actin filaments and its ability to create strong forces capable of completely deforming the structure.

In a second embodiment, the surface may have disposed thereon a pattern, more precisely a nano- or micro-pattern, comprising at least two dots comprising or made of the actin nucleation agent, the dots being at a distance suitable for allowing the interaction of the polymerized actin filaments from two adjacent dots. Preferably, the dots have a diameter of from 1 to 10 μm, preferably from 2 to 7 μm, more preferably about 5 μm. Preferably, the pattern comprises several dots, the dots being at a distance suitable for allowing the interaction of the polymerized actin filaments from two adjacent dots. Accordingly, the pattern may include at least 2, 3, 4, 5, 6, 7, 8, 9 or 10 dots, in particular 2 to 1,000 dots or 10 to 100 dots. Preferably, the distance between two adjacent dots is from 1 to 40 microns, for instance 1, 2, 5, 10, 15, 20, 25 or 30 microns, preferably 5, 10, 15 or 20 microns, more preferably of about 10 microns. In a preferred embodiment, the pattern is an array of dots. Preferably, the dots have the same diameter, and the geometry of the array is regular. Examples of arrays of dots are shown in FIG. 8. This kind of pattern provides a network of anti-parallel bundles. Such architecture of actin filaments networks may present a special interest in the electronics field.

The present invention is not limited to these particular patterns. Depending on the question of interest, one skilled in the art may design other patterns. Indeed, the contribution of the inventors is not limited thereto as they established for the first time that the form and the arrangement of the actin nucleation agents allows the control of the structures formed by the actin polymerization, namely parallel and anti-parallel actin filaments bundles of controlled position, length and orientation.

Surface

The surface may be any solid support having a sufficient area for disposing thereon a pattern of actin nucleation agent as disclosed herein, preferably a plurality of linear patterns, more preferably a plurality of addressable patterns. In some embodiments, the surface can be considered to be flat or planar, although the devices and methods of the invention can be used on curved or otherwise shaped surfaces.

In a preferred embodiment, the surface is planar or essentially planar. Accordingly, in this embodiment, the surface is not a bead, in particular beads having a diameter too small for offering an area sufficient for disposing thereon the patterns of actin nucleation agent as disclosed herein.

Any surface appropriate for binding the actin nucleation agent forming the pattern may be used in the devices and methods disclosed herein.

In a preferred embodiment, except the actin nucleation agent patterns, the surface is an inert surface. An example of an appropriate inert surface is a surface covered by a derivative of poly(ethylene glycol). However, one skilled in the art knows other alternatives to prepare an inert surface. For instance, the surface can be non-derivatized silanes or the surface may be coated by other molecules commonly used in immunology assays to reduce non-specific binding, such as non-fat milk, bovine serum albumin, and human serum albumin.

The surface can generally be any surface used for microscale or nanoscale applications. For instance, the surface can be silicon, strained silicon, polycrystalline silicon, silicon dioxide, germanium, gallium arsenic, glass, plastic, ceramic, or metal. In a preferred embodiment, the surface is glass.

In a preferred embodiment, the surface may be a support convenient for confocal, optical and/or fluorescence microscopies, and in particular epifluorescence and Total Internal Reflection Fluorescence (TIRF) microscopies, although the invention also contemplates supports denied of good optical qualities (e.g., suitable for electron microscopy). In a more preferred embodiment, the plate is glass, possibly covered with a thin layer of oxidized polystyrene. For example, a convenient plate according to the present invention is a coverslip or a slide. It can also be a plastic slide, plastic dish or Petri dish.

The present invention also relates to a system comprising several surfaces as defined above or a combination of a surface as defined above with other elements. Accordingly, the system with several surfaces forms a 3D structure. The surfaces are placed so that the growing actin filaments from the actin nucleation sites of each surface may interact with each other. The surfaces may be parallel to each other or may form an angle, for example, the adjacent sides of a well.

Methods for Preparing the Devices

The present invention relates to a method for preparing the surface as disclosed herein. In particular, the present invention relates to a method for patterning a surface with an isolated actin nucleation agent for obtaining the pattern as disclosed above. The methods comprise at least the step of preparing with the actin nucleation agent a linear pattern deposited on the surface, preferably a plurality of linear patterns, more preferably a plurality of addressable patterns.

For micro- and nano-patterning, various methods can be used, such as microcontact printing, photolithography, laser ablation, a UV-based micropatterning approach (Azioune et al., 2009), Dip Pen (Ginger et al., 2004), Atomic Force Microscopy ("AFM") subtraction (Wadu-Mesthrige et al., 2001), and plasma deposition. For example, for structures on the order of micrometers, micropatterning of the work surface by contact printing can be accomplished by pressing the work surface against a micropatterned stamp coated with the actin nucleating agent. Stamps for protein deposition are typically made using photolithography on polydimethylsiloxane ("PDMS") substrates following what is now standard practice. The stamp can be "inked" directly with the protein which will be either passively adsorbed, or may be covalently bound to the substrate using common procedures.

In particular, it is desirable that the pattern to be covered with the actin nucleation agent is free of the coating rendering the surface inert. There are a number of ways of accomplishing this. For example, the nucleating agent may be applied on the surface, and then the coating rendering the surface inert is applied. Alternatively, the surface can be covered with a removable material prior to contacting the surface with the coating rendering the surface inert and the material is removed, leaving the sites free of the coating with an actin nucleation agent. However, preferably, areas free of the coating material may be created at the pattern of actin nucleation agent by removing the coating at these sites. The coating material can be burned off with a laser, scraped or pushed away using an AFM needle used in contact mode, or removed by UV or plasma treatment through a protecting mask. A convenient protocol is detailed in the Examples section and illustrated in FIG. 1a.

Multiple patterns of actin nucleation agent may be positioned on a surface. Ordered arrays of patterns (and thereby filaments) can be provided by, for example, placing a series of patterns of actin nucleation agent in a desired array. Preferably the patterns of actin nucleation agents are sufficiently separated from each other on the surface so that the filament or filaments from one pattern do not reach the filament or filaments from another pattern of the array. The distance to separate pairs of patterns of actin nucleation sites can be readily determined.

Actin Nucleation Agent or Nucleation Promoting Factor

The actin nucleation agent is a protein or fragment thereof capable of initiating actin polymerization in the presence of actin monomer(s) and ATP, and optionally of additional elements. The actin nucleation agent is often called in the art a "Nucleation Promoting Factor" (NPF). In particular, the actin nucleation agent can be, for example, ActA (Actin assembly-inducing protein), IscA, RickA, WASp (Wiskott-Aldrich Syndrome Protein), N-WASP, SCAR (suppressor of cAR), a VCA domain (Verprolin-homology, Cofilin-homology, Acidic regions), a WA region or a pWA region. The actin nucleation agent also includes analogues (chimeric forms or mutants) and fragments thereof capable of initiating actin polymerization. The actin nucleation agents are disclosed in US 2006/0003399 and US2005/0106629, the disclosure thereof being incorporated herein by reference. Other suitable actin nucleation agents are also disclosed in Pollard et al., 2000 and Higgs and Pollard, 2001.

In addition to actin monomer(s) and ATP, the actin nucleation agent may further need other elements necessary for initiating actin polymerization, in particular Arp 2/3 complex and an actin filament. In particular, the actin nucleation agent is coated on the surface of the device whereas the other elements required for initiating the actin polymerization are provided in the polymerization solution or mix, in particular actin monomers, ATP, an actin filament and an Arp2/3 complex.

The actin nucleation agent further requires Arp (actin-related protein) 2/3 complex for initiating actin polymerization. The actin nucleation agent acts by changing the conformation of Arp2/3 complex to resemble an F-actin dimer, thereby initiating actin polymerization. Accordingly, actin polymerization is initiated in an Arp2/3-dependent manner.

Regarding the actin filament provided in the polymerization solution or mix, it is important to note that this actin filament is not elongated. Indeed, a ternary complex including the actin nucleation agent, Arp2/3 and the actin filament is formed. This ternary complex is then able to initiate the polymerization of actin filaments, the neo-synthesized filaments growing as branches of the actin filament of the ternary complex. Accordingly, from the initial actin filament, the nucleation agent will promote the polymerization of hundreds of actin filaments, thereby reaching a high density of growing actin filaments.

In addition, some actin nucleation agents like ActA, IscA, RickA, WASp, N-WASP and SCAR may require additional regulating proteins or elements (also called upstream regulators) such as Cdc42, PIP$_2$, Nck and Rac1. Those requirements are well-known in the art and, for instance, are detailed in US 2006/003399 and Higgs and Pollard, 2001.

In a preferred embodiment, the actin nucleation agent is pWA, the C-terminal domains from the WASP/Scar proteins. pWA includes the proline-rich domain, the actin monomer-binding W domain, and the p21-binding A domain of WASP or SCAR. In particular, pWA may comprise or consist of amino acids 172-559 of human Scar protein (SEQ ID NO: 1). The actin nucleation agent may also advantageously be the VCA domain.

Indeed, the use of the pWA or VCA domain is advantageous over the other actin nucleation agents because it does not involve the necessity of upstream regulators. In a more preferred embodiment, the actin nucleation agent is pWA (in particular, as disclosed with details in Machesky et al., 1999).

The actin nucleation agent may include one or several tag(s), preferably linked or fused to the amino and/or carboxyl terminal ends. The tags are utilized to improve expression, to improve solubility, to aid in purification and/or to facilitate the binding on the surface. A variety of tags can be used, including but are not limited to: 1) a glutathione S-transferase (GST) tag, which can be used to bind to glutathione-agarose; 2) a His6 tag (or simply a HIS tag), which can be used to bind to immobilized metal-ion columns (e.g., nickel); 3) a calmodulin-binding peptide (CBP) tag that binds calmodulin-agarose columns; 4) an epitope tag (e.g., a hemagglutinin tag, a myc tag, or a FLAG tag), which can be used to bind an antibody with specific binding affinity for the epitope tag; and 5) a maltose-binding protein (MBP) tag, which increases the solubility of fused proteins. These tags can also be used in combination, with one or more tags fused to the amino terminus and one or more additional tags fused to the carboxyl terminus. In a particular embodiment, the actin nucleation agent is pWA linked to two tags, in particular a GST tag and an His tag, more particularly a GST tag at its N-terminal end and an His tag at its C-terminal end. pWA with the two tags presents the sequence.

Polymerization Solution or Mix

The polymerization solution or mix comprises ingredients sufficient to induce and maintain actin polymerization. Requirement for the polymerization solution or mix is well-known in the art. In particular, one skilled in the art knows the appropriate concentrations of the polymerization mix components.

The polymerization solution or mix includes ATP, monomeric actin (G-actin), divalent cation and the Arp2/3 complex. Preferably, the polymerization solution or mix further includes an actin filament.

The methods for preparing purified monomeric actin have been well-known in the art for a long time (MacLean-Fletcher & Pollard, 1980; Spudich & Watt, 1971). Indeed, actin and its polymerization have been studied for almost fifty years. In addition, purified monomeric actin is also commercially available (e.g., Invitrogen Cat. No. A12375).

Preferably, the monomeric actin includes labeled monomeric actin. The monomeric actin is preferably labeled by a fluorescent protein or dye. Examples of fluorescent protein or dye include, but are not limited thereto, fluorescent dyes such as the Alexa Fluor dyes (e.g., Alexa 350, Alexa 430, Alexa 488, Alexa 532, Alexa 546, Alexa 568, and Alexa 594 dyes), cyanin dyes (e.g., Cy3 and Cy5), Texas Red, acyrolodan, pyrene and the like, and fluorescent proteins such as GFP, CFP, YFP, RFP and mCherry. Preferably, fluorescent dyes will be used. Some fluorescently labeled actin monomers are commercially available (e.g., non-exhaustively, Invitrogen: Alexa 488 conjugate (Cat. No.: A12373), Alexa 568 conjugate (Cat. No.: A12374), Alexa 594 conjugate (Cat. No.: A34050) and Alexa 647 conjugate (Cat. No.: A34051)). Other suitable fluorescent labels will be apparent to one of ordinary skill in the art. Preferably, the polymerization solution or mix comprises a mixture of labeled and non-labeled actin monomers.

In a particular embodiment, the monomeric actin may alternatively or further include monomeric actin bound to a metal atom, in particular to gold. Preparation of actin monomer(s) labeled with gold is detailed in Patolsky et al., 2004. The polymerization solution or mix may only include actin monomer(s) labeled with a metal atom, in particular with gold, or may include a mixture of unlabeled actin monomers and actin monomers labeled with a metal atom, in particular with gold.

The "Arp2/3 complex," first isolated from *Acanthamoeba castellani*, consists of seven polypeptides: two actin-related proteins, Arp2 and Arp3, and five other proteins, p40, p35, p19, p18, and p14. The human complex consists of seven subunits that include the actin-related proteins Arp2 and Arp3, and five others referred to as p41-Arc, p34-Arc, p21-Arc, p20-Arc, and p16-Arc. The predicted amino acid sequence of all seven subunits has been determined. The Arp2/3 complex in *Saccharomyces cerevisiae* consists of six subunits. Studies have determined that the nucleating and organizing activities of the complex are separable. Thus, not all the subunits of the Arp2/3 complex may be necessary for the nucleation activity contemplated by the methods of the invention. Accordingly, as used herein, references to the "Arp2/3 complex" refer to the full 6- or 7-component complex, or to assemblages of such components of the complex as are necessary to nucleate actin polymerization, unless reference to the full 6- or 7-protein complex is required by context. Any Arp2/3 complex from any origin may be conveniently used in the polymerization mix, methods and kits as disclosed herein. For instance, US 2006/0014266 discloses a method for purifying Arp2/3 complex (the disclosure of which is incorporated herein by reference).

Any actin filament is appropriate. For instance, the suitable actin filaments may have a length of 30-100 nm.

Preferably, the polymerization solution or mix further includes profilin. Indeed, profilin allows prevention of the spontaneous actin polymerization. The presence of profilin in the polymerization mix or solution is appropriate when the actin nucleation agent is pWA.

In a particular embodiment, the polymerization mix or solution may be a cell extract (Theriot et al., 1992) or an egg extract (e.g., xenopus extract) (Marchand et al., 1995).

Kits

The present invention relates to kits for preparing actin filaments, in particular with a determined organization, or for conducting the assay or screening methods.

The present invention also relates to a kit comprising a device as disclosed herein and an actin polymerization solution or mix comprising components sufficient to induce actin polymerization in the presence of the actin nucleation used on the device, in particular a polymerization mix as disclosed above. The kit may contain a leaflet explaining how to use the kit. The kit may further comprise control molecules with well-characterized effects on the actin filaments networks, interactions and/or structures. Such molecules may be myosin, alpha-actinin or fascin.

Uses and Methods

The device as disclosed herein is useful for preparing or manufacturing actin filaments networks, in particular with a reproducible (i.e., predictable) structure, organization and/or interactions of the actin filaments. Accordingly, the present invention relates to the use of the device as disclosed herein for preparing or manufacturing actin filaments networks. The present invention relates to methods for preparing or manufacturing actin filaments networks, in particular two- or three-dimensional actin structures. In particular, the present invention provides a method for preparing or manufacturing actin filaments networks comprising a) providing a device as disclosed herein; b) contacting said pattern, preferably said nano- or micro-pattern, with a polymerization solution or mix, thereby inducing polymerization of actin filaments; and optionally c) removing the polymerization solution or mix.

In a preferred embodiment, the method comprises one or several of the following embodiments: a) the actin nucleation agent is pWA; b) the surface is planar; and/or c) the polymerization mix includes actin monomer(s), ATP, divalent cation, an Arp2/3 complex, and preferably labeled actin monomer(s), preferably fluorescently labeled actin monomer(s) or actin monomer(s) bound to a metallic atom such as Au.

It is thought that the oriented growth of filaments out of nucleating regions, perpendicular to the nucleating region edge, results from filament-filament repulsion in a dense network. Low density of filaments would not result in an oriented growth out of the nucleating regions. When filaments are sufficiently packed, their steric repulsion induces their alignment perpendicular to the edge of the nucleating regions. In particular, it may be considered that a minimal density of actin filaments is 10 filaments by $\mu m^2$. Preferably, the density of actin filaments by $\mu m^2$ is at least 20, 30, 40 or 50. When the nucleating region is fully coated with NPF (nucleation promoting factor) (also called actin nucleation agent herein), pWA for example, the filament density only depends on the concentration of the Arp2/3 complex in the polymerization mix or solution. Nucleation is induced by the formation of a trimer of pWA-Arp2/3-actin filament. The actin monomers are used at a concentration suitable sufficient to induce and maintain actin polymerization (e.g., with a minimal concentration of 0.01 mg/ml). However, actin monomers are preferably used in large excess in the conditions allowing filament polymerization. So the formation of the trimer only depends on the presence of Arp2/3 complex. A concentration of 10 nM of Arp2/3 complex is not sufficient to induce the critical density of filaments allowing their parallel alignment during their growth. Above 30 nM of Arp2/3 complex, filaments are sufficiently dense to grow in a parallel fashion, perpendicular to the nucleating region edge. Therefore, the polymerization solution or mix which is contacted with the pattern of actin nucleation agent contains at least 30 nM of the Arp2/3 complex.

The method may further comprise a step of coating the actin filaments or a step of treating them. In particular, after actin polymerization or during actin polymerization, the actin filaments may be further treated or coated. Optionally, the further treatment or coating is carried out after removal of the polymerization solution.

In a first embodiment, the actin filaments are further treated with proteins cross-linking actin filaments. Indeed, this additional treatment may increase the strength of the structures formed by the actin filaments, in particular the actin bundles. It allows the preparation of more rigid structures. Numerous proteins are known that bind, bundle, or cross-link actin filaments in cells, as noted further below. For instance, the actin cross-linking proteins may be alpha-actinin, fascin, EF-1, Scruin, villin, dematin, fimbrin, spectrin, dystrophin, ABP 120 or filamin (Lodish et al., Molecular Cell Biology, W. H. Freeman and Company, N.Y., N.Y. (2000), Table 18.1). An exemplary cross-linking protein is fascin, which can be used to link each subunit in one filament with a subunit in a neighboring filament. (Matsudaira et al., 1994). Similarly, the protein alpha-actinin can be used to link filaments. Both fascin and alpha-actinin line the filaments in parallel and link the filaments, but fascin links them more tightly. The additional treatment with actin cross-linking proteins can be carried out by washing or immersing the actin structures in a solution comprising the linking protein. It can be carried once the actin polymerization is done or during the actin polymerization process. It has been observed that the treatment with a cross-linking protein such as fascin or alpha-actinin, in particular during the actin polymerization process, may modify the obtained structure or organization. For instance, addition of high amount of fascin (e.g., 100 nM) or alpha-actinin (e.g., 500 nM) during the actin polymerization process may prevent the formation of the parallel bundles because of the high rigidity of the parallel actin filaments for the actin nucleation sites (see Examples section and FIG. 6). In addition, the obtained effect may change dependent on the used amount of cross-linking proteins such as fascin or alpha-actinin (see Examples section and FIG. 6a).

In a second embodiment, the actin filaments are further treated with capping protein. Capping protein may be used to control the length of the actin filaments. Capping proteins are known in the art, for instance CAPZA1 (F-actin-capping protein subunit alpha-1) or CAPZB. In addition, the use of a combination of a capping protein and cofilin may lead to a dynamic structure, thereby maintaining growing actin filaments.

In a third embodiment, the actin filaments are further coated with a substance. In particular, the actin filaments may be coated with a conductive substance. Preferably, the conductive substance can be a metal atom, more preferably gold. Alternatively, the substance may be carbon nanotubes. In a particular embodiment, the actin filaments already contain actin conjugated with gold and the coating with gold allows the enhancement of gold deposition (e.g., see Patolsky et al., 2004). Thereby, the invention provides a method for preparing actin-based metal wire, in particular gold wires. Accordingly, the present invention relates to a method for preparing conductive micro- or nano-wires which can be useful in the fabrication of nanoscale circuitry, in particular in the field of the nanobiotechnology.

In addition, the present invention provides a method for preparing or manufacturing actin filaments, in particular with a determined organization, further comprising the removal of the obtained actin filaments from the surface. Optionally, the actin filaments may also be treated or coated as described above after their removal from the surface.

In another particular embodiment, the present invention provides a method for patterning a surface with a substance. In this method, the actin filaments on the surface are used as a mask for coating the surface with a substance. In particular, the method comprises a) providing a surfaced having thereon a nano- or micro-pattern of the invention, b) contacting said nano- or micro-pattern with a polymerization solution, thereby inducing polymerization of actin filaments, c) coating the surface with the substance, and d) removing the actin filaments from the surface (e.g., by depolymerization of the actin filaments), thereby leaving the substance coated on the surface with the desired pattern. For instance, coating of the surface may be carried out by chemical vapor deposition. The substance may be selected from silicon, polysilicon, silicon dioxide, carbon fiber, carbon nanofibers, filaments, carbon nanotubes, $SiO_2$, silicon-germanium, tungsten, silicon carbide, silicon nitride, silicon oxynitride, titanium nitride, metals and various high-k dielectrics. Alternatively, the coating may be carried out by spin coating and the substance may be a polymer, such as polystyrene or a more polar polymer such as a polysulfone orpolyetherimide. It can also be used for preparing photopolymer film resist.

In an alternative particular embodiment, the present invention provides a method for etching a surface with a substance. In this method, the actin filaments on the surface are used as a mask for etching the surface with a substance. In particular, the method comprises a) providing a surfaced having thereon a nano- or micro-pattern of the invention, b) contacting said nano- or micro-pattern with a polymerization solution, thereby inducing polymerization of actin filaments, c) etching the surface, and d) removing the actin filaments from the surface (e.g., by depolymerization of the actin filaments). Indeed, the actin filaments serve as a mask to cover the surface while the surface not covered with the actin filaments is etched. For example, in chip manufacturing, a thin metal film is typically deposited on a semiconductor, such as silicon, the metal is masked in a desired pattern, and the non-masked metal is etched away. The methods of the present invention permit masking a desired pattern on the metal layer with actin filaments, and then etching the metal not masked by the actin filaments.

The patterns of the invention, in particular the nano- or micro-patterns, are useful for studying actin filaments interactions and/or for studying actin filaments network structures. Accordingly, the present invention relates the use of the device as disclosed herein for studying actin filaments interactions and/or for studying actin filaments network structures. The present invention further relates to a method for studying actin filaments interactions and/or for studying actin filaments network structures, wherein the method comprises the preparation or the manufacture of actin filaments as disclosed above. In particular, the method comprises a) providing a device as disclosed herein; b) contacting said pattern, preferably said nano- or micro-pattern, with a polymerization solution or mix, thereby inducing polymerization of actin filaments; and c) observing the structure and/or interactions of the actin filaments. In particular, the observation step may include observing the growth of the actin filaments and their organization. The observation can be carried out at one particular moment, at successive particular moments or by a video. The interactions of the actin filaments may be parallel or antiparallel. The formation of particular structures may be observed, such as the formation of bundles of actin filaments. Once the actin filaments are polymerized, one can also study actin depolymerization.

The actin filaments and their organization may be preferably observed by fluorescence microscopy. Therefore, the actin filaments may be labeled by using fluorescently labeled actin monomer(s) during polymerization step or the actin filaments may be labeled once polymerized with fluorescently labeled phalloidin. Several fluorescently labeled phalloidins are commercially available (e.g., Rhodamine-phalloidin (Molecular Probes); Texas red-phalloidin (Molecular Probes).

During step b), between step b) and c), or during step c), the micropattern may be further contacted with other molecules or conditions, in particular for studying the impact of these other molecules or conditions on the actin polymerization, actin filaments interactions and/or actin filaments network or network structure.

The device as disclosed may also be used for assessing or determining the effect of a test molecule on the actin filaments interactions and/or actin filaments network structure. Accordingly, the present invention relates to the use of the device as disclosed herein for assessing or determining the effect of a test molecule on the actin filaments interactions and/or actin filaments network structure. The present invention also concerns a method for determining if a test molecule modulates the actin filaments interactions and/or the actin filaments network or network structure, wherein the method comprises the preparation or the manufacture of actin filaments as disclosed above, contacting the actin filaments with the test molecule, and determining the effect of the test molecule on the actin polymerization, the actin filaments interactions and/or the actin filaments network or network structure. In particular, the method comprises a) providing a nano- or micro-pattern of the invention, b) contacting said micro-pattern with a polymerization solution, and c) observing the structure and/or interactions of the actin filaments, thereby determining if the test molecule modulates the actin filaments interactions and/or the actin filaments network structure, wherein the test molecule is added before, during the actin polymerization and/or after the actin polymerization. In a preferred embodiment, the test molecule is added during the actin polymerization, for instance simultaneously with the polymerization mix or solution. In an alternative preferred embodiment, the test molecule is added once the actin filaments are polymerized, for instance after the removal of the polymerization mix or solution. Preferably, the observed actin filaments interactions and/or actin filaments network or network structure in the presence of the test molecule is compared to the observed actin filaments interactions and/or actin filaments network or network structure in the absence of the test molecule. The advantage of the patterns as disclosed herein is that the actin filaments interactions and the actin filaments network structures obtained with the device of the invention are reproducible. Therefore, the comparison of the actin polymerization, the actin filaments interactions and the actin filaments network structures in the presence and in the absence of a test molecule is possible and accurate.

The test molecule may be of various origins, natures and compositions. It may be any organic or inorganic substance, such as a lipid, peptide, polypeptide, nucleic acid, small molecule, drug, etc., in isolation or in mixture with other substances. For instance, the test compound can be an antibody, an antisense oligonucleotide, or an RNAi. The molecule may be all or part of a combinatorial library of products.

By "modulate" is intended that the test molecule may inhibit or activate the actin polymerization. Alternatively, the test molecule may also disturb the actin filament organization, in particular the actin filaments interactions and the actin filaments network or network structure.

In the Examples section, the effect of some molecules on the actin polymerization and on the polymerized actin filaments has been tested with the device as disclosed above (see FIG. 6 wherein the effect of alpha-actinin and fascin has been studied). It can be observed that the patterns of the invention, by providing reproducible and predictable actin filaments organization, allow the observation of the effect of test molecules on the actin filaments organization. In particular, the effect may be observed during the actin polymerization, but also once the actin filaments are polymerized and organized by the selected patterns.

The method for assessing or determining the effect of a test molecule on the actin polymerization, actin filaments interactions and/or actin filaments network or network structure presents several utilities.

In a first particular embodiment, this method may be used for screening molecules and identifying the test molecules which are able or not to modulate the actin polymerization, the actin filaments interactions and/or the actin filaments network or network structure, depending on the effect sought. The screening methods disclosed herein allows the identification of molecules which may be useful, when the molecule exhibits inhibitor activity for actin polymerization, for treating tumor metastasis, thrombosis or osteoporosis, or for inhibiting angiogenesis, and when the molecule exhibits activator activity for actin polymerization, for improving wound healing or for promoting neurogenesis.

In a second embodiment, this method may be used for evaluating the toxicity of a molecule, in particular the actin-toxicity of a molecule. This toxicity may be evaluated by the capacity of the molecule to inhibit the actin polymerization or the actin depolymerization, or to prevent normal actin filament network formation.

The device as disclosed may also be used for assessing or determining the effect of a particular cell extract on the actin filaments interactions and/or actin filaments network structure. Accordingly, the present invention relates to the use of the device as disclosed herein for assessing or determining the effect of a particular cell extract on the actin filaments interactions and/or actin filaments network structure. The present invention also concerns a method for determining if a particular cell extract modulates the actin filaments interactions and/or the actin filaments network or network structure, wherein the method comprises the preparation or manufacture of actin filaments as disclosed above with the particular cell extract, and determining the effect of the particular cell extract on the actin polymerization, the actin filaments interactions and/or the actin filaments network or network structure by comparing with a reference cell extract. In particular, the method comprises a) providing a nano- or micro-pattern of the invention, b) contacting said micro-pattern with a particular cell extract, and c) observing the structure and/or interactions of the actin filaments by comparing with a reference cell extract, thereby determining if the particular cell extract modulates the actin filaments interactions and/or the actin filaments network structure. The advantage of the patterns as disclosed herein is that the actin filaments interactions and the actin filaments network structures obtained with the device of the invention are reproducible. Therefore, the comparison of the actin polymerization, the actin filaments interactions and the actin filaments network structures in the presence of a particular cell extract and in comparison with a reference cell extract is possible and accurate. In particular, the reference cell extract comes from a healthy cell and the particular cell extract comes from a cell having a defect, in particular a defect related to actin filaments.

The present invention is also convenient for studying molecular motors, such as myosins. Molecular motors may be added in the polymerization mix or may be added on the surface with already polymerized actin filaments. By the action of molecular motors, the actin structure is bent or distorted. By studying the deformation of the actin structures, by defining the order of areas of deformation, and by measuring the deformation velocity and orientation, one can investigate how the molecular motors interact with the actin filaments. In addition, the present invention also provides a method for identifying the molecules able to modulate the molecular motor's activity or the interaction between the molecular motor and the actin filaments. Without the device as disclosed herein, the in vitro study of molecular motors is very difficult or impossible and this study is generally limited to the cellular context wherein the structures are unpredictable and complex. In addition to the complex structure in the cellular context, a high number of proteins interacting with actins are also present. Therefore, in this complex, clearly identifiable and measurable deformations of actin filaments cannot be observed and quantified. Similarly, by studying molecular motors in gel or other actin structures, it is impossible or difficult to compare the structure before and after molecular motor interaction because the actin filaments network structures are random, therefore all different and non-comparable. The device of the present invention allows these drawbacks to be overcome and the convenient study of molecular motors.

Definition

The origin of the proteins used in the present invention has no impact. Proteins of any source may be used and, in particular, proteins of variable sources may be used together.

As used herein, the term "about" means +/−10%, preferably +/−5%. Of course, this term, when associated with a value, may be removed and the exact value is always contemplated herein.

Further aspects and advantages of the present invention will be disclosed in the following Examples section, which should be regarded as illustrative and not limiting the scope of the present application.

Examples

Actin filaments constitute one of the main components of the cell cytoskeleton. Specific actin cytoskeleton structures, such as branched networks or parallel filament bundles, power definite cellular functions. Biochemical reconstitution of actin network assembly from purified proteins, in bulk solution or with biomimetic devices, has been a powerful tool to circumvent cell complexity and decipher molecular mechanisms governing actin assembly. These approaches have highlighted how actin-binding proteins affect the growth and the interactions of actin filaments within dynamic networks. However, the question of how geometric boundaries, such as the ones encountered in cells, affect the dynamic formation of highly ordered actin structures remains largely unstudied.

Here, the inventors demonstrate that the nucleation geometry in itself can be the principal determinant of actin network architecture. They developed a micropatterning method that allows the spatial control of actin nucleation sites for in vitro assays. In particular, they modulated the positioning of nucleation sites at scales corresponding to cellular dimensions. Shape, orientation and distance between nucleation regions control filament orientation and length, filament-filament interactions and filopodia-like bundle formation. Modeling of filament growth and interactions demonstrated that basic mechanical and probabilistic laws govern actin assembly in higher-order structures.

Figure 1B:
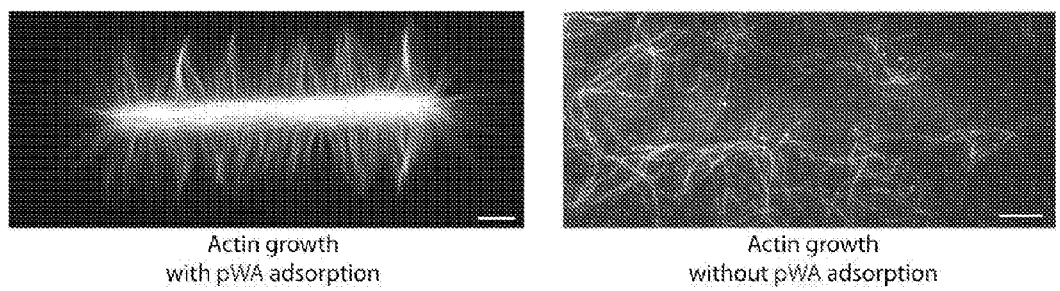
Figure 1C:
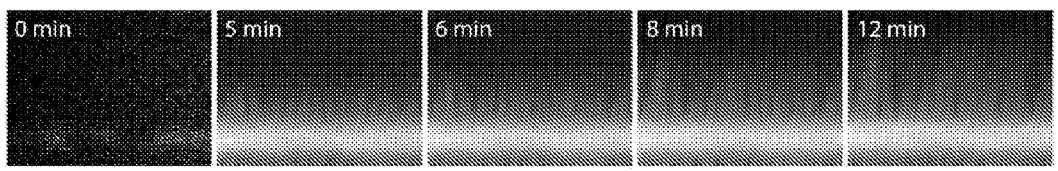
FIG. 1c, actin filament nucleation and growth on a pWA-coated micropattern.
Figure 1D:
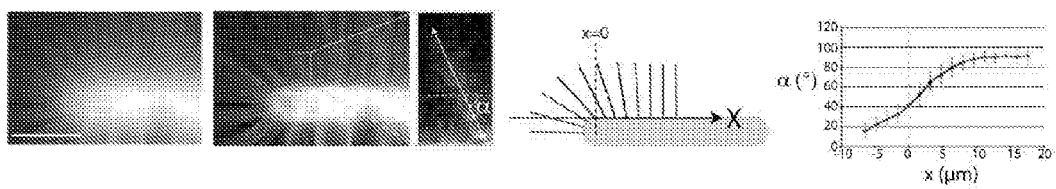
FIG. 1d, the fluorescence image was filtered and the angle between actin filament and the bar micropattern major axis manually measured with respect to their position (x) along the bar. Scale bars indicate 10 μm.
Figure 2A:
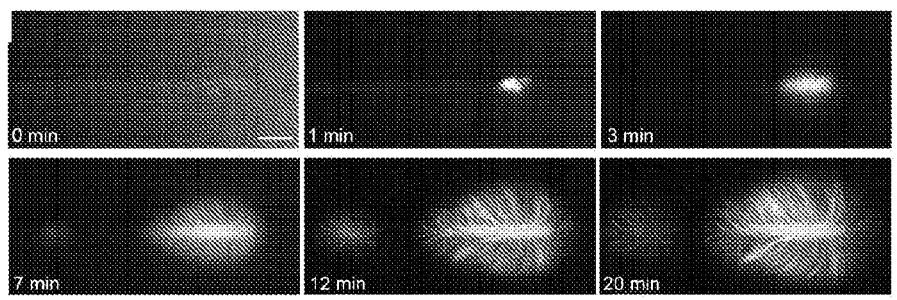
FIGS. 2a-2g: Biochemical control of filament number and length.
Figure 2B:
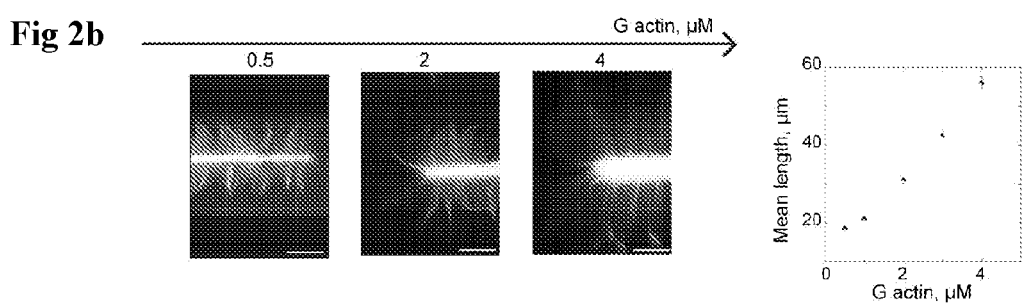
Figure 2C:
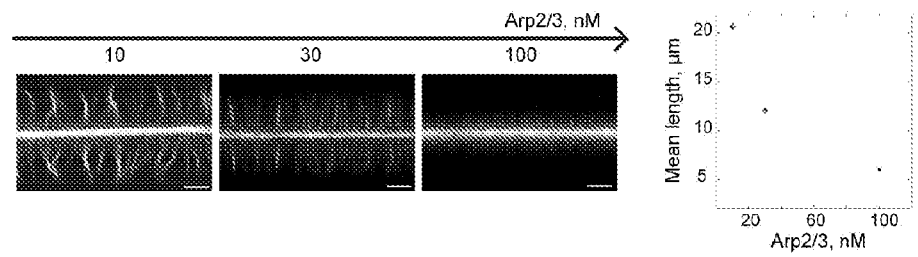
Figure 2D:
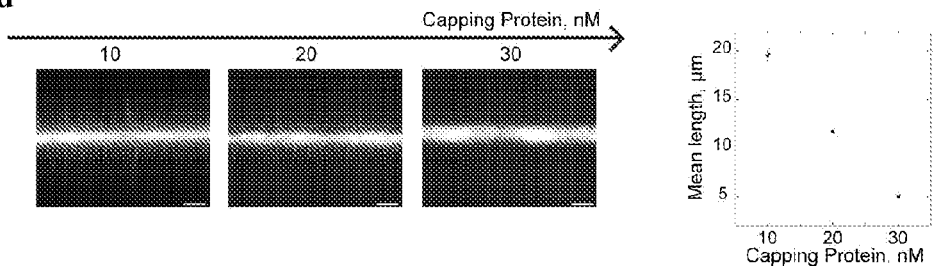
Figure 2E:
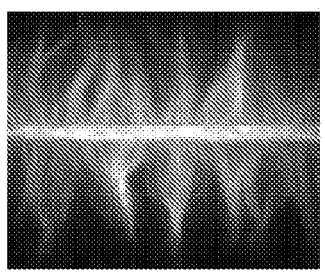
Figure 2F:
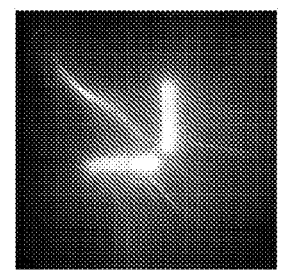
Figure 2G:
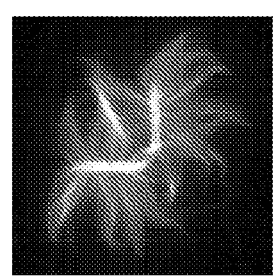

As a first step and to precisely regulate the position of actin nucleation sites in vitro, the inventors used a recently developed UV-based micropatterning approach (Azioune et al., 2009) to create a template for the localization of the Nucleation Promoting Factor (NPF), pWA (FIG. 1a). pWA (SEQ ID NO: 1) comprises the C-terminal domains from the WASP/Scar proteins, a ubiquitous family of proteins that initiate actin polymerization on a preexisting actin filament in the presence of the Arp2/3 complex and an actin monomer (Blanchoin et al., 2000; Machesky et al., 1999; Mullins et al., 1998). A small volume of solution made of a minimal set of purified proteins actin polymerization (2 µM actin monomers (7% labeled with Alexa 568), 6 µM profilin and 30 nM Arp2/3 complex) was placed between the pWA-coated micropatterned slide and a glass support. Functionalized micropatterns specifically initiate actin filament nucleation on their surface and promote 2D growth of actin filaments (FIG. 1b). As a control, the inventors demonstrated that in the absence of pWA coating, a bar-shaped micropattern does not recruit any actin filaments spontaneously assembled in the solution (FIG. 1b). This confirms that functionalized micropatterns specifically initiate actin filament nucleation on their surface. Real-time visualization of actin filament nucleation and growth highlighted the autocatalytic process of network formation (FIG. 2). These networks were generated by filaments growing from the pWA-coated regions, with their fast-growing, barbed-end oriented outwards (FIG. 1c). In agreement with actin filament growth on glass rods, as the nucleation waves propagate, dense and interconnected networks were formed on the micropattern (FIG. 2). Collectively, actin filaments emanating from this dense meshwork self-organized normally to the micropattern edge, except within the narrow region close to the bar end (FIG. 1c-d). Although densely organized into a parallel network, these filaments could be further gathered into larger bundles by the addition of cross-linking factors, the inventors therefore referred to as "filaments" rather than "bundles". The inventors termed "bundles" the structures unaffected by the subsequent addition of cross-linkers (see FIG. 6). They validated that filament growth on the micropattern was sensitive to known biochemical parameters: filament length increased with the concentration of G-actin, and decreased with increasing concentrations of Arp2/3 or capping protein, and bundled by α-actinin or fascin (FIG. 2).

Figure 3A:
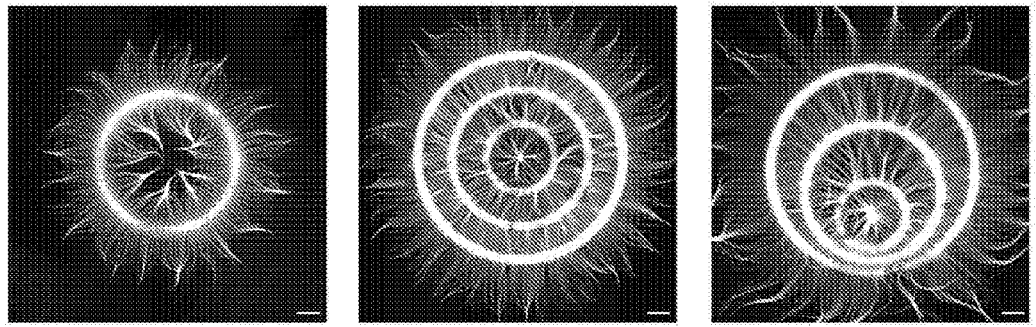
FIGS. 3a-3b: Filaments' length controls their ability to cross dense actin networks.
Figure 3B:
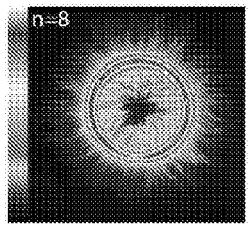
Figure 3B:
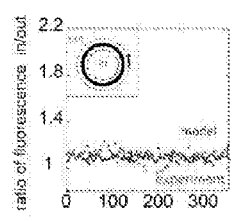
Figure 3B:
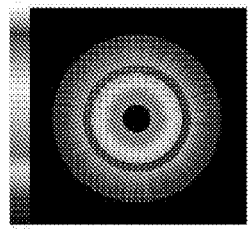
Figure 3B:
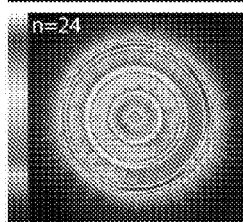
Figure 3B:
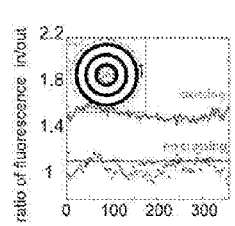
Figure 3B:
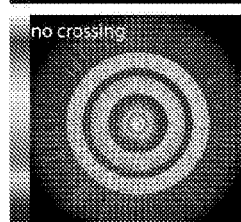
Figure 3B:
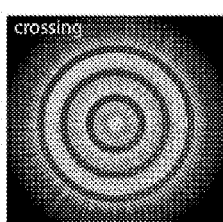
Figure 3B:
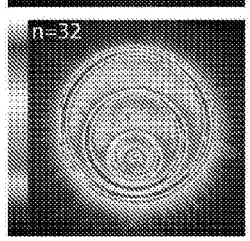
Figure 3B:
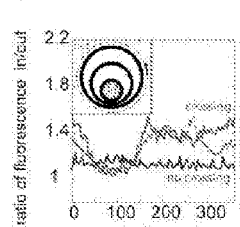
Figure 3B:
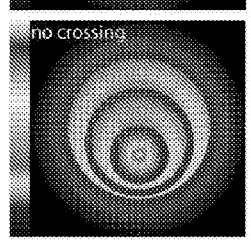
Figure 3B:
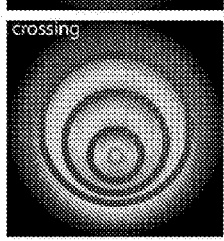

The inventors took advantage of the geometric control of actin growth to investigate the interaction between two sets of actin filaments growing toward each other. They therefore analyzed actin growth from individual, concentric or eccentric circles. Twenty- to thirty-micron long actin filaments grew radially inwards and outwards (FIG. 3a). Surprisingly, the networks generated by three concentric circles spaced 15 microns apart did not simply superimpose and the centripetal arrangement of parallel bundles disappeared. Instead, the interactions between inward- and outward-growing filaments formed short and thin anti-parallel bundles between adjacent circles. Interestingly, actin filament elongation seemed to be blocked by the presence of the dense actin network formed on the adjacent circles. To verify this, the inventors quantified the local actin network density by averaging several images taken separately on identical micropatterns (FIG. 3b). In addition, to understand how actin filament growth could lead to these actin density profiles, they performed numerical simulations, where actin filaments were nucleated with a constant linear density along the circle. Filaments grew normally out of the circle and their length was determined by the biochemical conditions. Actin filaments were then allowed or not allowed to cross adjacent nucleation regions, and theoretical density maps were derived from the local density of simulated actin filaments (FIG. 3b). Numerical simulations showed that on concentric circles, filaments did not cross the dense network region lying on their path. Conversely, when the distance between separate nucleation regions was reduced, as in the case of eccentric circles, the density within the inner circle was no longer isotropic. Numerical simulations confirmed that additional filaments enter this innermost region to locally increase fluorescence intensity (FIG. 3b). This demonstrated that short, and thus stiff, filaments can grow through the dense network, whereas longer and more flexible filaments get entangled and blocked by an adjacent actin network. Consequently, physical constraints in addition to biochemical cues regulate actin filament length.

Figure 4A:
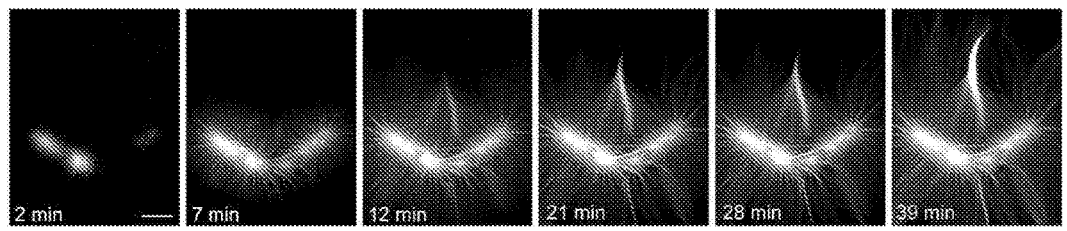
FIGS. 4a-4d: Orientation of nucleation regions controls bundle formation.
Figure 4B:
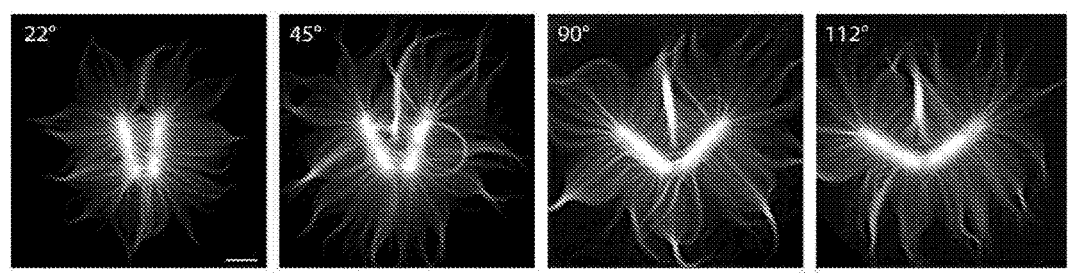
Figure 4C:
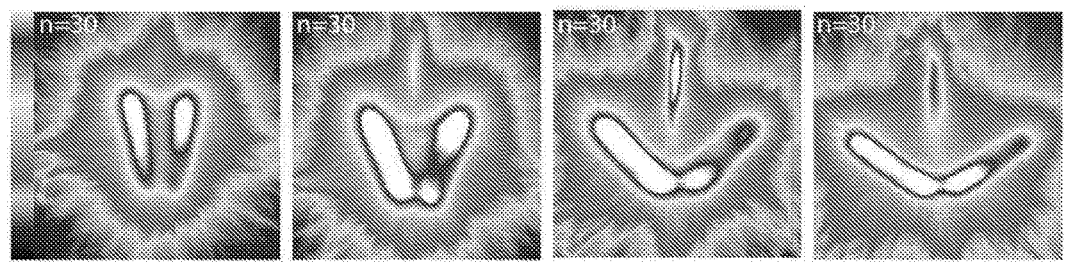
Figure 4D:
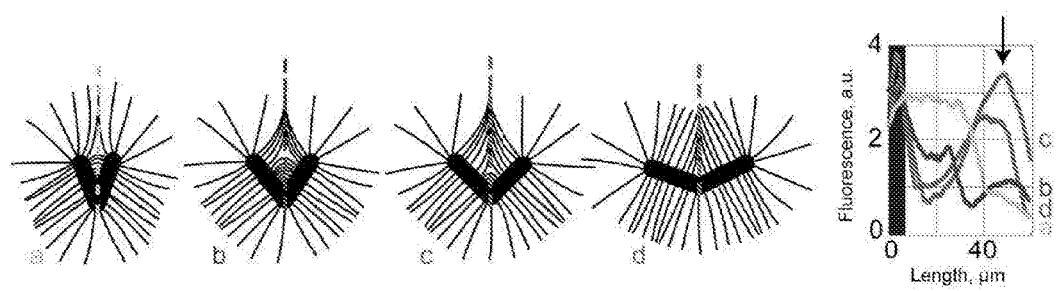

To further explore the role of geometric parameters on actin filament interactions and their resulting network structure, the inventors forced contacts between filaments at various angles. When nucleated from two short bars, filaments first grew perpendicularly to the bars, then interacted and zippered to form a filopodia-like parallel bundle (FIG. 4a, FIG. 7), reminiscent of that present in vivo. This interaction forced the filaments to bend, so bundle formation depended on filaments' ability to change their growing direction. We tested this parameter by varying the angle between the two short bars (FIG. 4b) and quantified the formation of parallel bundles (FIG. 4c). For nucleation bar angles close to 22°, filaments are associated into short and thin anti-parallel bundles. Parallel bundles only started to form above a critical angle between 22° and 45°, and averaged image analysis confirmed the existence of an optimal angle to promote the coalescence of numerous filaments into a parallel bundle (FIG. 4d).

Figure 5A:
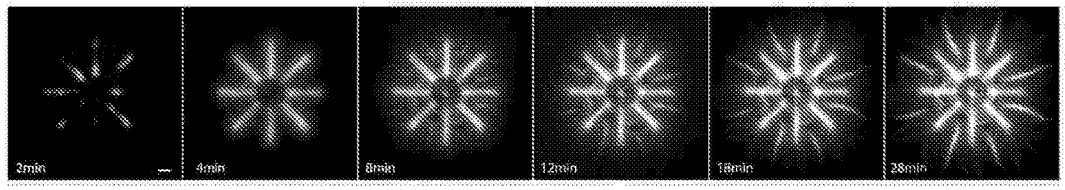
Figure 5B:
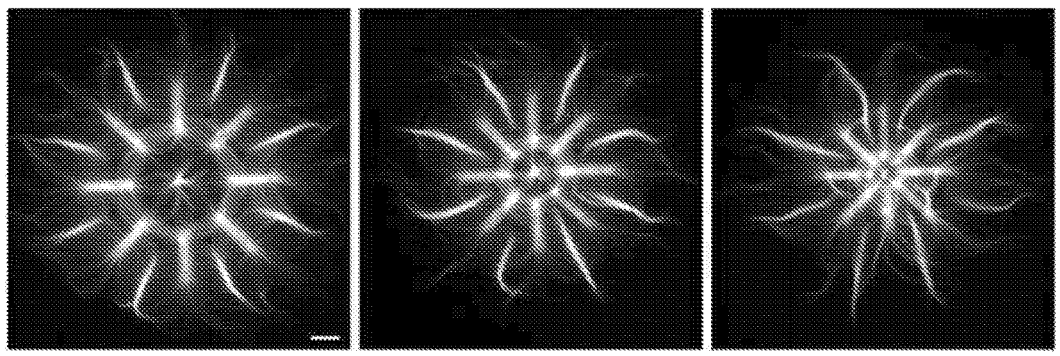
Figure 5C:
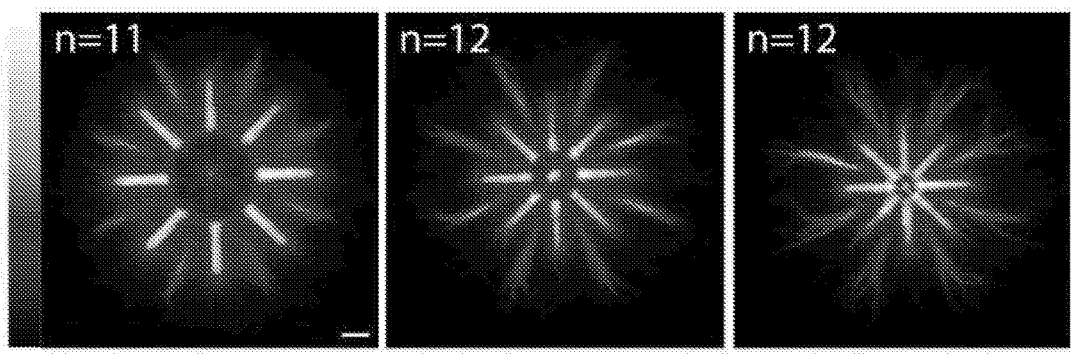
Figure 5D:
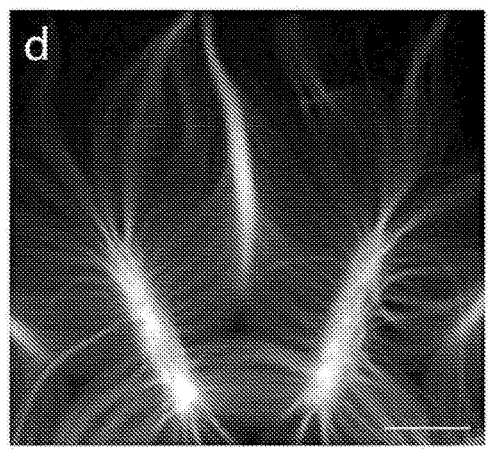

Since the inventors demonstrated that the length and rigidity of filaments modulate their interaction with actin filament networks, they investigated whether or not a variation in the distance at a given angle between two nucleation regions would affect bundle formation. For this purpose they designed eight-branched radial arrays where the rays were moved in and out from the origin. As expected, filaments grew outward from each ray and formed parallel bundles on the bisecting line between adjacent rays (FIGS. 5a-b and FIG. 7). When rays where sufficiently distant, short parallel bundles formed precisely along the bisecting line and maintained this orientation. As the distance between rays decreased, bundles were longer, mis-positioned and curved (FIGS. 5b-c). In all cases, the transition between the assembly of anti-parallel bundles in the proximal part of the rays and the assembly of parallel bundles in their distal part occurred at a quite variable position (FIGS. 5d-e). Consequently, the distance between nucleation sites, in the range tested, was not critical to the generation of the final structure. The position of the transition from anti-parallel to parallel bundles could be modeled as the result of intrinsic filament properties and collective assembly (FIG. 5f). If filaments assemble exclusively into anti-parallel bundles in the proximal part of the network, filaments that contact each other have a probability p to assemble into parallel bundles. This intrinsic probability p depends only on filament orientation and therefore on their position along the ray (FIG. 1d). If filaments form a parallel bundle in the proximal network, the encountering filaments are forced to bend and contribute to this parallel bundle. Therefore the probability Q to form a parallel bundle is given by:

$$Q(y+1) = p(y)(1-Q(y)) + Q(y) \quad (1)$$

which reads:

$$Q(y) = 1 - \prod_{k=0}^{y-1} (1 - p(k)) \quad (2)$$

where y is a discrete variable characterizing the position along the bisecting axis. The transition positions obtained from the probability function Q precisely matched experimental data (FIG. 5g). Since a transition point generates a parallel bundle made of all distal filaments, the inventors calculated the bundle size and fluorescent intensity associated with each transition point. The model accurately accounted for both the increase of fluorescence due to filament assembly into the bundle and the reduction of fluorescence due to various filament lengths within the bundle (FIG. 5h). These geometrically mediated bundles still occur in the presence of two distinct actin cross-linkers in a concentration-dependent manner (FIG. 6). This confirms that bundle emergence is tightly controlled by the mechanical properties of the actin filament.

The reconstitution of the filopodia-like bundles as performed by the inventors relies on the spontaneous formation of a precursor structure formed by the collapse and the further coalescence of actin filaments emanating from the dense actin network, to which adjacent elongating filaments will systematically converge. Interestingly, this propagative coalescence of actin filaments initiated by a precursor, like the A-precursors corresponding to the splayed filopodial roots observed in vivo, accounts for the emergence of the parallel bundles from the dense surrounding network in cells. Moreover, this propagative process explains the presence of short actin filaments within bundles, consistent with the high barbed-end capping activity present at the leading edge of lamellipodia.

The present innovative methodology demonstrated that, independently of the mixture of actin-binding proteins, nucleation geometry plays a key role in the determination of the actin filament network architecture. Respective positioning of adjacent nucleation zones results in the entanglement of actin filaments into networks and the control of their length. Actin filament orientation determines their ability to interact with neighbors and to form bundles. Fundamentally, basic mechanical and probabilistic laws govern the spatial arrangements of anti-parallel and filopodia-like parallel filaments in response to defined geometric boundary conditions. By extension to living cells, this work emphasizes the importance of the spatial and temporal organization of the nucleation areas, giving rise to specific actin network architectures and hence controlling the location of force production. Although the spatio-temporal regulation of actin growth is known to influence cell shape, the present work has revealed, in quantitative terms, that reciprocally physical boundaries, within or around the cell, control actin cytoskeleton architectures.

Materials and Methods

Protein expression and purification: Actin was purified from rabbit skeletal-muscle acetone powder (MacLean-Fletcher & Pollard, 1980; Spudich & Watt, 1971). Actin was labeled on lysines with Alexa 488 according to Isambert et al. (1995). Arp2/3 complex was purified from bovine brain extracts as according to Egile et al. (1999). GST-pWA, human profilin, and mouse capping protein were expressed and purified as described previously (Almo et al., 1994; Falck et al., 2004; Machesky et al., 1999).

Micropatterning: Glass coverslips were oxidized with oxygen plasma (10 s, 30 W, Harrick Plasma, Ithaca, N.Y.) and incubated with 0.1 mg/ml of polylysine-L-g-polyethylene glycol (PLL-PEG) (JenKem Technology, TX) in HEPES 10 mM at pH 7.4 for 1 h. Pegylated coverslips were placed on a chromium synthetic quartz photomask (Toppan Photomasks, Corbeil, France) using a homemade vacuum holder. The chromium layer of the photomask contained 3 μm wide transparent micropatterns. The mask-covered coverslips were then exposed to deep UV light (1<200 nm, UVO Cleaner, Jelight Company, Irvine, Calif.) for 5 min and coated with a solution of the Nucleation Promoting Factor pWA at 0.5 μM for 15 min.

Actin polymerization: Protein mixtures were diluted in freshly prepared fluorescence buffer containing 10 mM imidazole-HCl (pH 7.8), 50 mM KCl, 1 mM $MgCl_2$, 100 mM dithiothreitol, 3 mg/ml glucose, 20 μg/ml catalase, 100 mg/ml glucose oxidase and 0.5% methylcellulose to induce actin polymerization. Actin polymerization was induced in a solution containing 2 μM actin monomers (7% labeled with Alexa 568 or Alexa 488), 6 μM profilin and 30 nM Arp2/3 complex.

Image acquisition: Images were taken using a straight BX61 Olympus microscope equipped with a 40× dry objective (UPLFLN, NA=0.75), an XY motorized stage (Marzhauser, Germany) and a CoolSNAP HQ2 camera (Roper Scientific, GmbH, Germany). Microscope and devices were driven by MetaMorph (Molecular Devices, Downingtown, Pa.).

Image treatment: All images were taken using the same light intensity and exposure time. However, before being overlaid and averaged, images' grey scales were adjusted to have the same minimum and maximum grey values. Displayed images were filtered using the "unsharp mask" and the "Gaussian blur" filters from ImageJ software to highlight filaments from the background.

Total Internal Reflection Fluorescence microscopy: Total Internal Reflection Fluorescence acquisitions were performed on a Nikon TE2000E inverted microscope equipped with a 50 mW 488 nm laser and a QuantEM 512SC—Quantitative EMCCD camera (Roper Scientific).

REFERENCES

Almo et al., 1994, *J Mol Biol* 236, 950-952.
Azioune et al., 2009, *Lab Chip* 9, 1640-1642.
Blanchoin et al., 2000, *Nature* 404, 1007-1011.
DeLaCruz et al., 2001, *J Blol Chem* 276, 32373-32381.
Egile et al., 1999, *J Cell Biol* 146, 1319-1332.

Falck et al., 2004, *EMBO J* 23, 3010-3019.
Ginger et al., 2004, *Angew Chem Int Ed Engl* 43, 30-45.
Haraszti et al., 2009, *Chemphyschem* 10, 2777-86.
Higgs H N, Pollard T D, 2001, *Annu Rev Biochem* 70:649-76.
Isambert et al., 1995, *J Biol Chem* 270, 11437-11444.
MacLean-Fletcher & Pollard, 1980, *Cell* 20, 329-341.
Machesky et al., 1999, *Proc Natl Acad Sci USA* 96, 3739-3744.
Marchand et al., 1995, *J Cell Biol* 130, 331-43.
Matsudaira et al., 1994, *Semin Cell Biol* 5, 165-74.
Michelot et al., 2007, *Current Biology* 17, 825-833.
Mullins et al., 1998, *Proc Natl Acad Sci USA* 95, 6181-6186.
Patolsky et al., 2004, *Nature Materials* 3, 692-695.
Pollard et al., 2000, *Annu Rev Biophys Biomol Struct* 29, 545-76.
Roos et al., 2003, *ChemPhysChem*, 4, 872-877.
Spudich & Watt, 1971, *J Blol Chem* 246, 4866-4871.
Theriot et al., 1992, *Nature* 357, 257-60.
Uhrig et al., 2009, *Lab On A Chip*, 9, 661-668.
Wadu-Mesthrige et al., 2001, *Biophys J* 80, 1891-9.

The invention claimed is:

1. A device for preparing an actin filament network by contacting a pattern on said device with an actin polymerization solution comprising actin monomer(s), ATP, divalent cations, an actin filament and an Arp2/3 complex, the device comprising a surface having disposed thereon a pattern comprising a line comprising an actin nucleation agent or a pattern comprising at least two dots, wherein each dot comprises an actin nucleation agent, the dots are at a distance suitable for allowing the interaction of the polymerized actin filaments from two adjacent dots and the dots are at a distance ranging from 1 µm to 40 µm, wherein the actin nucleation agent is selected from the group consisting of members of the WASP/SCAR family, pWA fragments thereof, VCA domains thereof, ActA, IscA and C-terminal regions thereof, and wherein the surface is devoid of any actin capture site disposed thereon.

2. The device according to claim 1, wherein the surface has disposed thereon a plurality of patterns.

3. The device according to claim 1, wherein the pattern comprises several dots or lines, the dots or lines being at a distance suitable for allowing the interaction of the polymerized actin filaments from two adjacent dots or lines.

4. The device according to claim 1, wherein the pattern comprises:
one circle or several nested circles; and/or
two or more lines; and/or
an array of dots.

5. The device according to claim 1, wherein the pattern comprises two to five circles, said circles having different diameters and being concentric or eccentric, and the smaller circles being contained within the bigger circles.

6. The device according to claim 1, wherein the pattern comprises two or more lines, the lines forming with respect to each other:
an angle of less than or no more than 25°;
an angle of more than 25° and less than 110°; or
an angle of more than 110° and less than 150°.

7. The device according to claim 1, wherein said pattern includes several lines arranged so as to form a radial pattern.

8. The device according to claim 1, wherein the surface is planar.

9. A kit comprising a device as defined in claim 1 and an actin polymerization solution comprising components sufficient to induce actin polymerization, the components being selected from one or more of: actin monomer(s), ATP, divalent cations, an actin filament, an Arp2/3 complex, and profilin.

10. A method for preparing an actin filament network comprising:
a) providing a device comprising a surface having disposed thereon a pattern comprising a line comprising an actin nucleation agent or a pattern comprising at least two dots, wherein each dot comprises an actin nucleation agent, the dots are at a distance suitable for allowing the interaction of the polymerized actin filaments from two adjacent dots and the dots are at a distance ranging from 1 µm to 40 µm, wherein the actin nucleation agent is selected from the group consisting of members of the WASP/SCAR family, pWA fragments thereof, VCA domains thereof, ActA, IscA and C-terminal regions thereof; and
b) contacting said pattern with an actin polymerization solution comprising actin monomer(s), ATP, divalent cations, an actin filament and an Arp2/3 complex, thereby inducing polymerization of actin filaments and obtaining said actin filament network by self-organization of actin filaments, wherein the structure of the final actin filament network is controlled by the geometry of the pattern of the actin nucleation agent.

11. The method according to claim 10, wherein the method comprises:
coating the actin filaments with a conductive substance; and/or
treating the actin filaments with an actin cross-linking agent.

12. The method according to claim 10, wherein the polymerization solution contains at least 30 nM of the Arp2/3 complex.

13. The method according to claim 10, said method further comprising determining the spatial organization of actin filament networks formed on said device, the structure of said actin filament networks being controlled by the geometry of the pattern of the actin nucleation agent.

14. The method according to claim 13, wherein the polymerization solution contains at least 30 nM of the Arp2/3 complex.

15. A method for screening a test molecule for its capacity to modulate the actin filament networks, wherein the method comprises: a) providing a device comprising a surface having disposed thereon a pattern comprising a line comprising an actin nucleation agent or a pattern comprising at least two dots, wherein each dot comprises an actin nucleation agent, the dots are at a distance suitable for allowing the interaction of the polymerized actin filaments from two adjacent dots and the dots are at a distance ranging from 1 µm to 40 µm, wherein the actin nucleation agent is selected from the group consisting of members of the WASP/SCAR family, pWA fragments thereof, VCA domains thereof, ActA, IscA and C-terminal regions thereof; b) contacting said pattern with a polymerization solution or mix comprising actin monomer(s), ATP, divalent cation, an actin filament and a Arp2/3 complex, thereby inducing polymerization of actin filaments and obtaining an actin filament network formed by self-organization of actin filaments, wherein the structure of the final actin filament network is controlled by the geometry of the pattern of actin nucleation agent; and c) observing the actin filament network, wherein the test molecule is added to the device before, during and/or after the actin polymerization and wherein the effect of the test molecule on the actin filament network is determined.

16. The method according to claim 15, wherein the actin polymerization solution contains at least 30 nM of the Arp2/3 complex.

17. The method according to claim 10, said method further comprising adding a molecular motor before, during and/or after the actin polymerization and determining the structure, the interactions and/or the deformation of the polymerized actin filaments formed on said device.

18. The device according to claim 1, wherein the surface has disposed thereon a plurality of patterns that are addressable.

19. The device according to claim 1, wherein the pattern comprises:
one circle or several nested circles; and/or
two or more lines.

20. The device according to claim 1, wherein the pattern is a micro-pattern or a nano-pattern.

21. The method according to claim 10, wherein the actin filament network comprises parallel actin filaments, anti-parallel actin filaments or a bundle of actin filaments.

22. The method according to claim 10, the method further comprising a step c) of removing the actin polymerization solution and/or removing the actin filaments obtained from the surface.

23. The method according to claim 10, wherein said device is devoid of any capture site.

* * * * *

```
                        SEQUENCE LISTING

<160> NUMBER OF SEQ ID NOS: 1

<210> SEQ ID NO 1
<211> LENGTH: 388
<212> TYPE: PRT
<213> ORGANISM: Homo sapiens

<400> SEQUENCE: 1

Lys Arg Lys Glu Lys Arg Lys Gln Lys Gln Lys Asn Leu Asp Arg Pro
1               5                   10                  15

His Glu Pro Glu Lys Val Pro Arg Ala Pro His Asp Arg Arg Arg Glu
            20                  25                  30

Trp Gln Lys Leu Ala Gln Gly Pro Glu Leu Ala Glu Asp Asp Ala Asn
        35                  40                  45

Leu Leu His Lys His Ile Glu Val Ala Asn Gly Pro Ala Ser His Phe
    50                  55                  60

Glu Thr Arg Pro Gln Thr Tyr Val Asp His Met Asp Gly Ser Tyr Ser
65                  70                  75                  80

Leu Ser Ala Leu Pro Phe Ser Gln Met Ser Glu Leu Leu Thr Arg Ala
                85                  90                  95

Glu Glu Arg Val Leu Val Arg Pro His Glu Pro Pro Pro Pro Pro Pro
            100                 105                 110

Met His Gly Ala Gly Asp Ala Lys Pro Ile Pro Thr Cys Ile Ser Ser
        115                 120                 125

Ala Thr Gly Leu Ile Glu Asn Arg Pro Gln Ser Pro Ala Thr Gly Arg
    130                 135                 140

Thr Pro Val Phe Val Ser Pro Thr Pro Pro Pro Pro Pro Pro Pro Leu
145                 150                 155                 160

Pro Ser Ala Leu Ser Thr Ser Ser Leu Arg Ala Ser Met Thr Ser Thr
                165                 170                 175

Pro Pro Pro Pro Val Pro Pro Pro Pro Pro Pro Ala Thr Ala Leu
            180                 185                 190

Gln Ala Pro Ala Val Pro Pro Pro Ala Pro Leu Gln Ile Ala Pro
        195                 200                 205

Gly Val Leu His Pro Ala Pro Pro Ile Ala Pro Leu Val Gln
    210                 215                 220

Pro Ser Pro Pro Val Ala Arg Ala Ala Pro Val Cys Glu Thr Val Pro
225                 230                 235                 240

Val His Pro Leu Pro Gln Gly Glu Val Gln Gly Leu Pro Pro Pro
                245                 250                 255

Pro Pro Pro Pro Leu Pro Pro Gly Ile Arg Pro Ser Ser Pro Val
            260                 265                 270

Thr Val Thr Ala Leu Ala His Pro Ser Gly Leu His Pro Thr Pro
        275                 280                 285

Ser Thr Ala Pro Gly Pro His Val Pro Leu Met Pro Pro Ser Pro Pro
```

```
                290                 295                 300

Ser Gln Val Ile Pro Ala Ser Glu Pro Lys Arg His Pro Ser Thr Leu
305                 310                 315                 320

Pro Val Ile Ser Asp Ala Arg Ser Val Leu Leu Glu Ala Ile Arg Lys
                325                 330                 335

Gly Ile Gln Leu Arg Lys Val Glu Glu Gln Arg Glu Gln Glu Ala Lys
                340                 345                 350

His Glu Arg Ile Glu Asn Asp Val Ala Thr Ile Leu Ser Arg Arg Ile
                355                 360                 365

Ala Val Glu Tyr Ser Asp Ser Glu Asp Asp Ser Glu Phe Asp Glu Val
                370                 375                 380

Asp Trp Leu Glu
385
```